(12) United States Patent
Salisbury et al.

(10) Patent No.: US 8,259,170 B2
(45) Date of Patent: Sep. 4, 2012

(54) INTEGRATED CALIBRATION SAMPLE BAY FOR FLUORESCENCE READERS

(75) Inventors: Richard C. Salisbury, Sewickley, PA (US); Dirk John VandenBerg, III, Pittsburgh, PA (US); Kim Anthony Ippolito, South Park, PA (US)

(73) Assignee: Cellomics, Inc., Pittsburgh, PA (US)

( * ) Notice: Subject to any disclaimer, the term of this patent is extended or adjusted under 35 U.S.C. 154(b) by 427 days.

(21) Appl. No.: 12/546,465

(22) Filed: Aug. 24, 2009

(65) Prior Publication Data

US 2011/0043618 A1  Feb. 24, 2011

(51) Int. Cl.
*H04N 7/18* (2006.01)
(52) U.S. Cl. ........... 348/79; 359/391; 359/392; 359/398
(58) Field of Classification Search .................... 348/79; 359/391, 392, 398
See application file for complete search history.

(56) References Cited

U.S. PATENT DOCUMENTS

| | | | |
|---|---|---|---|
| 6,075,613 A | 6/2000 | Schermer et al. | |
| 6,259,524 B1 * | 7/2001 | Hofstraat et al. | 356/243.4 |
| 6,348,965 B1 | 2/2002 | Palladino et al. | |
| 6,905,881 B2 | 6/2005 | Sammack et al. | |
| 2007/0081078 A1 * | 4/2007 | Cummings et al. | 348/79 |
| 2008/0180793 A1 | 7/2008 | Salisbury et al. | |
| 2009/0147355 A1 * | 6/2009 | Jennings | 359/391 |

FOREIGN PATENT DOCUMENTS

| | | |
|---|---|---|
| JP | 2005-278599 | 10/2005 |
| WO | WO 98/49537 | 11/1998 |
| WO | WO 00/04304 | 1/2000 |
| WO | WO 2009/075969 | 6/2009 |

OTHER PUBLICATIONS

PCT/US2010/040208, Oct. 6, 2010, International Search Report and Written Opinion.

* cited by examiner

*Primary Examiner* — Yves Dalencourt
(74) *Attorney, Agent, or Firm* — Workman Nydegger

(57) ABSTRACT

A stage assembly, an imaging system that uses the stage assembly, and methods for using the stage assembly in a high content screening system. The stage assembly includes a stage having a top surface and an opposing bottom surface and an opening extending between the top and bottom surfaces to receive a specimen plate. The stage assembly also includes a calibration sample bay formed in the stage. A calibration sample can also be secured within the calibration sample bay.

28 Claims, 15 Drawing Sheets

US 8,259,170 B2

INTEGRATED CALIBRATION SAMPLE BAY FOR FLUORESCENCE READERS

BACKGROUND OF THE INVENTION

1. The Field of the Invention

The present invention relates to apparatus and methods of high-content screening using imaging systems. More specifically, the present invention relates to calibration of such imaging systems.

2. The Relevant Technology

High-content screening ("HCS") is a cell-based screening method that yields detailed information about the temporal-spatial dynamics of cell constituents and processes, and plays an important role in the use of cell-based screening for identification and validation of drug candidates. The information provided by HCS alleviates bottlenecks in the drug discovery process by providing deep biological information. The assays associated with this method use either fixed or live cells, depending on the biological information desired.

In one method of performing an HCS scan, the cells of interest are loaded into an array of wells in a standard specimen plate (also known as a titer or microtiter plate) with 96 wells. The specimen plate is then positioned in a plate holder on a stage within an imaging system so that the specimen plate can move horizontally with the stage. The imaging system also includes a microscope. Motors are attached to the stage so that the stage and the specimen plate can be moved with respect to the microscopy in both directions orthogonal to the microscope. As a result, any of the individual wells can be positioned in alignment with the microscope so as to be able to be imaged through the microscope objective.

During a typical scan, the stage is moved by the motors until one of the wells is aligned with the objective and one or more of the cells within that well are imaged through the objective. The entire well can be imaged at the same time, or various fields within the well can be individually imaged. To image the different fields within the well, the stage is moved into different positions by the motors so that the objective is aligned with each field. When imaging is completed for the well, the stage is then moved by the motors until another one of the wells is aligned with the objective and, similar to the previous well, one or more of the cells within the newly aligned well are imaged through the objective. This movement and imaging of each individual well continues until all of the wells have been imaged through the objective. Computerized analysis is then performed on the obtained images to determine information about the cells. This type of scanning can be performed many times a day for different HCS scans using the same machine. It would be a benefit to be able to easily check the machine either during an HCS scan or between HCS scans to quickly determine if any of the system parameters are outside of predetermined limits and need to be calibrated.

Furthermore, often, a single HCS scan will require more than the 96 cell samples available on the standard specimen plate. In those cases, more than one specimen plate of cells is used to determine information about the cells. To accomplish this, each specimen plate must be separately scanned, either in separate imaging systems or one after the other in the same imaging system. When using multiple specimen plates, it is desirous to compare the different HCS scans performed within the same or different imaging systems.

For the results of these different scans to be comparable, local differences in the imaging systems and software associated with the optics, illumination, geometry of the plate, or other assay-specific parameters, must be minimized to ensure reproducibility and value of the information derived from performing HCS.

Currently, calibration of an imaging system consists of using a custom plate or placing various calibration samples within various wells of a standard 96-well specimen plate, placing the custom plate or specimen plate within the plate holder, and imaging the plate similar to when performing an HCS scan. This is tedious and time consuming and can lead to potential errors and discrepancies. For example, loading and unloading a custom or specimen plate within an imaging system takes a finite amount of time that adds up when performing many HCS scans and calibrations. Furthermore, because the calibration requires loading and unloading a new plate each time, automation of the calibration process is not available. Finally, the user of the imaging system must be extremely careful to load up the calibration plate in exactly the same way each time and on each imaging system to be able to obtain the same calibration results. Otherwise, various discrepancies can occur. Because of the difficulties noted above and others, most imaging systems are calibrated only rarely by the end user.

Accordingly, it would be an improvement in the art to provide an imaging system that solves some or all of the above problems and/or other limitations known in the art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
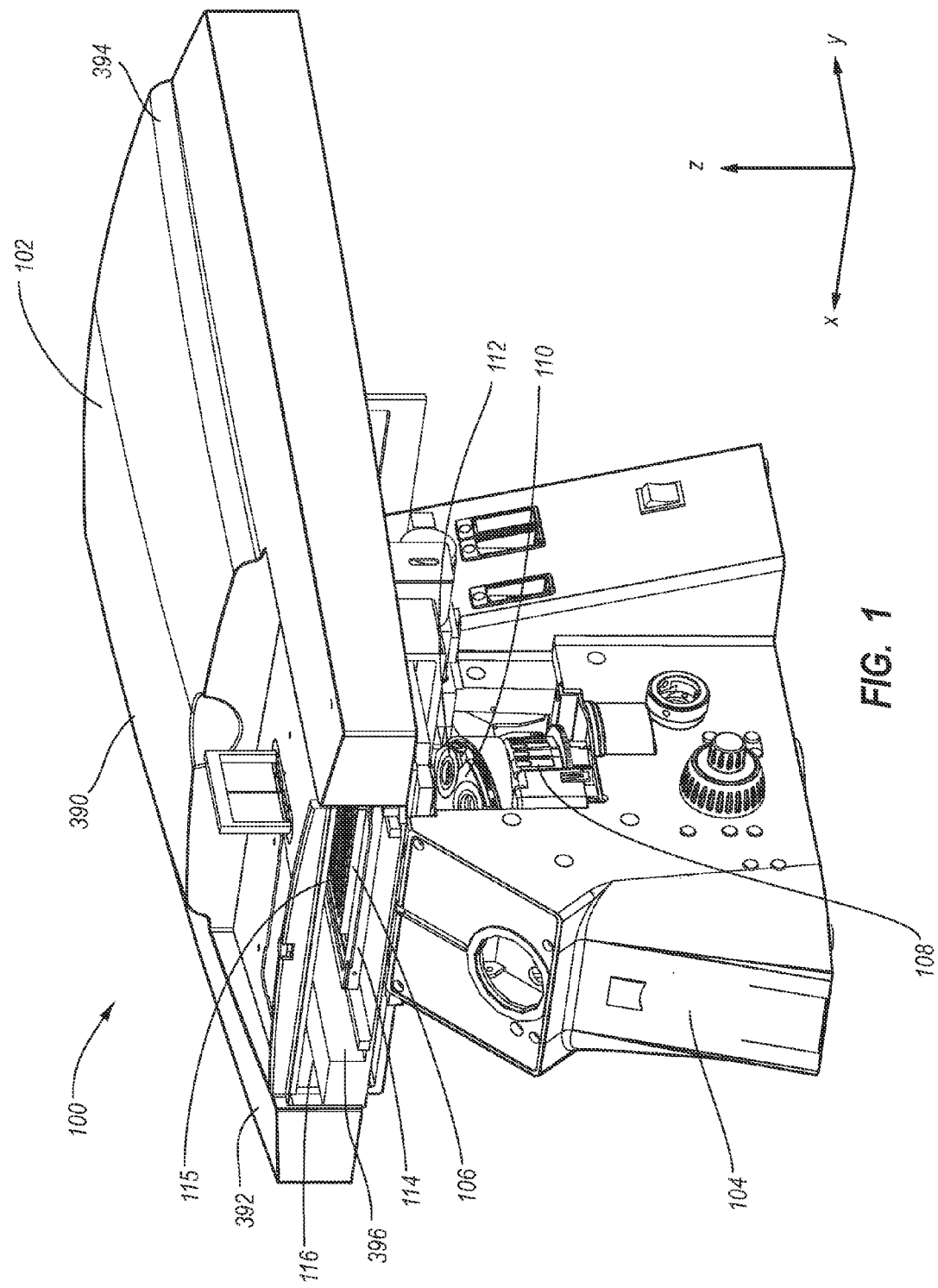
FIG. 1 is a front perspective view of an imaging system used for HCS with a stage assembly inserted into a recess therein.

Depicted in FIG. 1 is one embodiment of an imaging system 100 incorporating features of the present invention. Imaging system 100 is used to scan and analyze biological cells using high content screening.

Imaging system 100 comprises a stage housing 102 mounted on a microscope assembly 104. In general, stage housing 102 houses components required to position a specimen plate 106 containing biological cells so microscope assembly 104 can perform high content screening of the biological cells.

Stage housing 102 comprises a housing 390 extending from a first end 392 to a spaced apart second end 394 and bounding a compartment 396. A slot 116 that communicates with compartment 396 is formed on the first end 392 of housing 390.

Microscope assembly 104 houses an inverted microscope 108 that can be used to perform screening of cells from underneath the cells. Although the discussion herein is geared toward the use of an inverted microscope, it is appreciated that a non-inverted microscope can alternatively be used to perform screening of cells from above the cells.

Microscope 108 includes an objective 109 (see FIG. 4) through which the cells are viewed and a lens assembly 110 with one or more lenses 112 that can be moved up or down (with respect to microscope assembly 104) or rotated by microscope 108 so as to align and focus any one of the lenses 112 through the objective 109 on the biological cells disposed within the specimen plate 106 above the lens 112. Many conventional inverted microscopes can be used as microscope 108. For example, microscope Axiovert 200M manufactured by Carl Zeiss MicroImaging, Inc. in Goettingin, Germany can be used in embodiments of the current invention.

Figure 2:
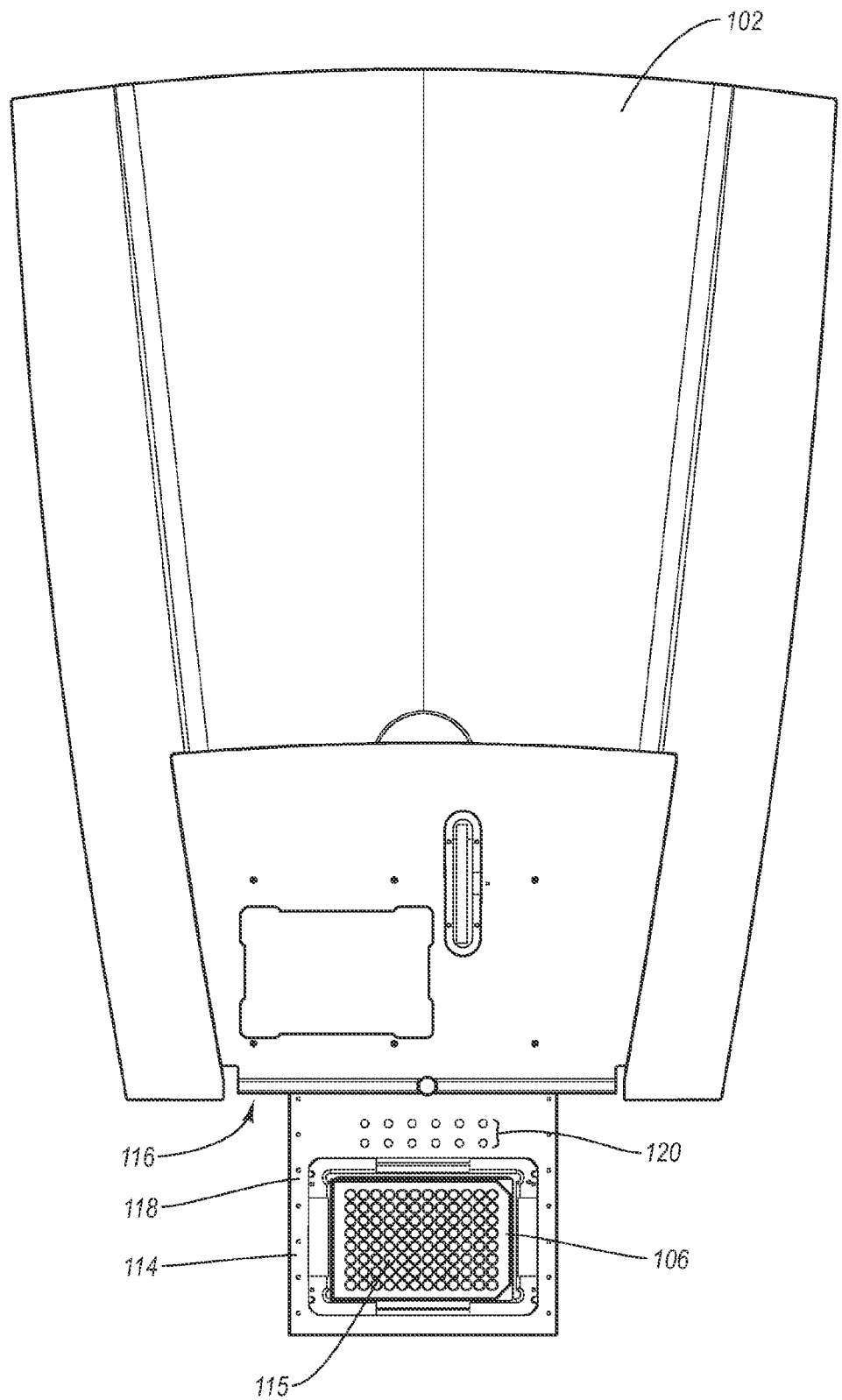
FIG. 2 is a top perspective view of the HCS system shown in FIG. 1 with the stage assembly outwardly extending from the recess.

A stage assembly 114 that is adapted to receive and hold specimen plate 106, is movably disposed within stage housing 102. Stage assembly 114 can be selectively moved between a retracted position and an extended position. In the retracted position, stage assembly 114 is disposed within compartment 396 of stage housing 102 over microscope 108. In the extended position, at least a portion of stage assembly 114 projects out from compartment 396 through slot 116 in stage housing 102 so as to be openly exposed. FIG. 1 depicts the stage assembly 114 in the retracted position while FIG. 2 depicts the stage assembly 114 in the extended position.

Alternatively, instead of a slot 116, housing 390 can incorporate an opening on top of housing 390 through which specimen plate 106 can be dropped onto stage assembly 114. In this embodiment, stage assembly 114 does not get moved to an extended position, but remains within the compartment 396 while specimen plate is positioned thereon. One or more doors can be positioned over the opening to prevent extraneous light from entering compartment 396 during use, if desired.

Throughout the document, reference is made to x, y, and z directions. As shown in FIG. 1, the y direction is defined as the horizontal direction in which stage assembly 114 is inserted into and extracted from slot 116, and the x direction is defined as the horizontal direction that is orthogonal to the y direction. The y direction can also be referred to as the proximal and distal direction and the x direction can also be referred to as the lateral direction. The z direction is defined as the vertical direction that is orthogonal to both x and y directions.

Figure 3:
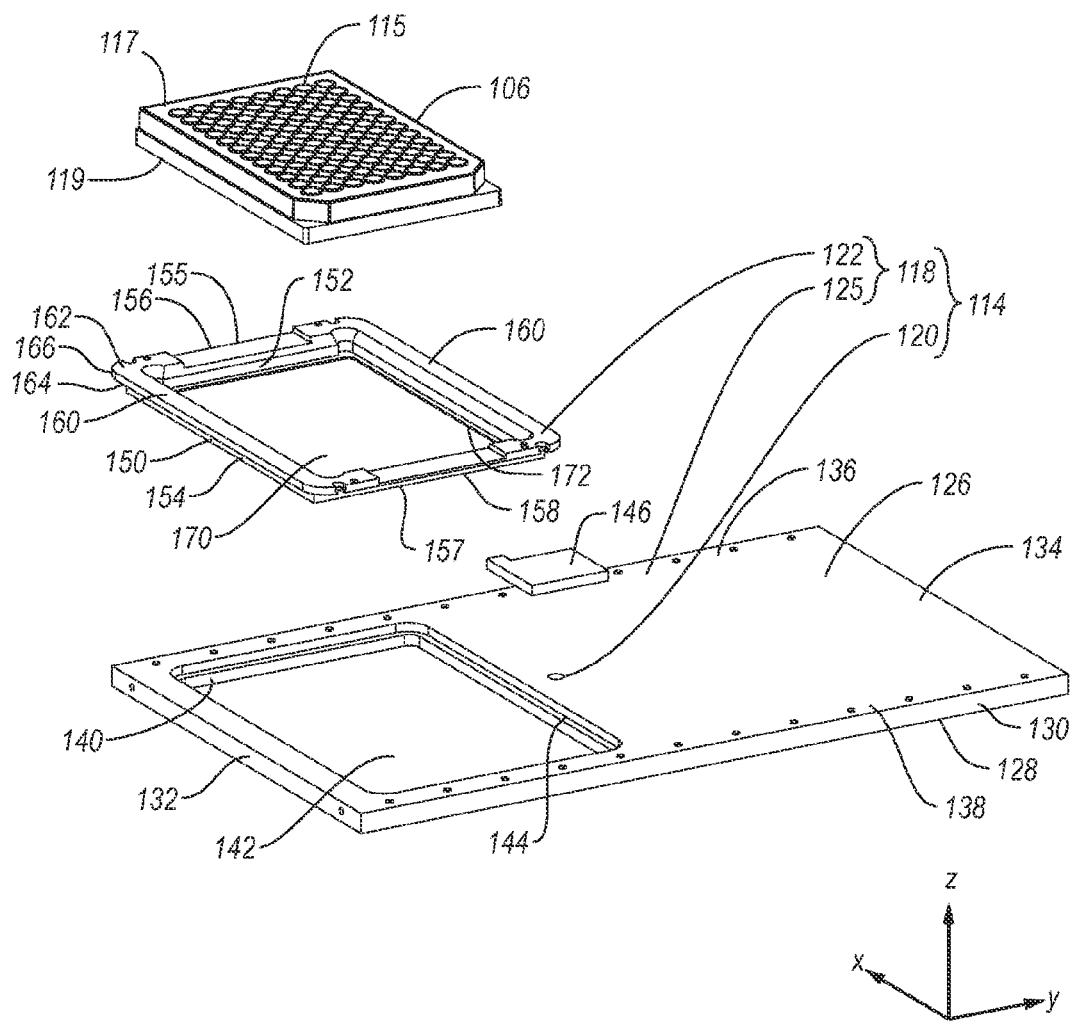
FIG. 3 is an exploded perspective view of the stage assembly and specimen plate used in the imaging system shown in FIG. 1.

As noted above, stage assembly 114 is configured to receive specimen plate 106 holding biological cells. Turning to FIG. 3, specimen plate 106 has a top surface 117 and an opposing bottom surface 119 with a plurality of spaced apart wells 115 formed on top surface 117. The wells 115 extend through specimen plate 106 so as be able to receive and hold biological cells while allowing light from the cells to pass through the bottom of the wells 115 and be imaged from below the specimen plate 106. To facilitate this, specimen plate 106 is comprised of polystyrene, polypropylene, other polymers, glass, or other material as is known in the art. In addition, glass plates and glass or plastic slides can alternatively be used.

The number of wells 115 formed within specimen plate 106 can vary. In the depicted embodiment, specimen plate 106 comprises a standard 96-well plate, as is known in the art. Specimen plates having more or less wells, as is known in the art, can alternatively be used. For example, a specimen plate having 384 wells as is known in the art can used. Furthermore, other types of specimen plates as is known in the art can also be used. For example, slides, chamber slides or other types of plates can alternatively be used.

Continuing with FIG. 3, stage assembly 114 comprises a stage 118 and one or more calibration sample bays 120 configured to receive calibration samples that are used to aid in calibrating the imaging system, as discussed in more detail below. Stage assembly 114 is adapted to be mounted on a stage moving assembly 124 (see FIG. 5) that can move stage assembly 114 two-dimensionally (the x and y directions shown in FIG. 3) while stage assembly 114 is disposed within stage housing 102 in the retracted position discussed above.

Stage 118 comprises a main body 125 and a specimen plate holder 122 mounted thereon. Main body 125, typically in the form of an elongated plate, has a top surface 126 and an opposing bottom surface 128 with a perimeter sidewall 130 extending therebetween. Stage plate 125 extends between a proximal end 132 and an opposing distal end 134, and between a first lateral side 136 and a second lateral side 138. Stage plate 125 also has an interior sidewall 140 that bounds an opening 142 extending all the way through stage plate 125 from top surface 126 to bottom surface 128 at proximal end 132. A shoulder 144 that extends into opening 142 is formed on interior sidewall 140. Opening 142 is sized to receive specimen plate holder 122 without allowing specimen plate holder 122 to pass completely through opening 142.

One or more engaging devices, such as engaging member 146, may also be included in or on stage plate 125 to engage with the motors that move stage assembly 114, as is known in the art.

Continuing with FIG. 3, specimen plate holder 122 is configured to be received within opening 142 of stage plate 125 and to removably receive and position specimen plate 106 holding biological cells for scanning. Specimen plate holder 122 has a perimeter sidewall 150 having an interior surface 152 and an opposing exterior surface 154 that each extend from an upper surface 155 at an upper end 156 to a lower surface 157 at a lower end 158.

To aid in mounting onto stage plate 125, one or more outwardly extending lips 160 are disposed on upper end 156 of sidewall 150. Lips 160 have an upper surface 162 and an opposing lower surface 164 that extend out over exterior surface 154 in a substantially orthogonal direction to an outer edge 166. Although in the depicted embodiment a plurality of lips 160 are shown positioned along sidewall 150, it is appreciated that a single continuous lip 160 can alternatively be used that extends along the entire length of sidewall 150 or any portion thereof. In some embodiments, upper surface 162 of lip 160 is also the upper surface 155 of the specimen plate holder 122.

Interior surface 152 of perimeter sidewall 150 bounds a compartment 170 that passes all the way through specimen plate holder 122 from upper end 156 to lower end 158. As noted above, specimen plate holder 122 is configured to removably receive, hold, and position specimen plate 106. Towards this end, an inwardly extending lip 172 is disposed on lower end 158 of interior surface 152 so as to at least partially encircle compartment 158. Lip 172 extends away from interior surface 152 into compartment 158 and is sized to allow specimen plate 106 to rest on lip 172 when specimen plate 106 is disposed on stage plate 125. Although not shown, specimen plate holder 122 also includes means for securely positioning specimen plate 106 within specimen plate holder 122, such as a lever or other device as is known in the art.

Figure 4:
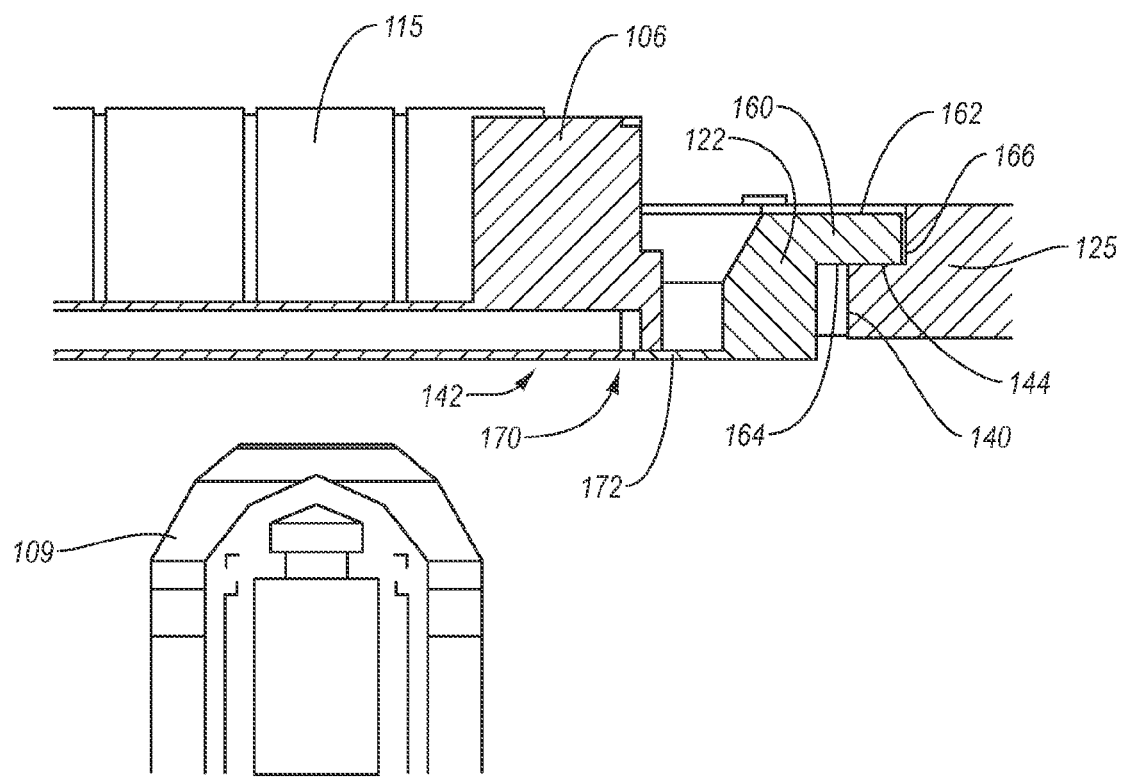
FIG. 4 is a cross sectional side view of a portion of the stage assembly and specimen plate shown in FIG. 3, with the specimen plate positioned on the stage assembly and an objective of a microscope positioned below the specimen plate.

Turning to FIG. 4, when stage 118 is assembled, specimen plate holder 122 is received within opening 142 of stage plate 125 such that lower surface 164 of lip 160 rests on shoulder 144 of interior sidewall 140 of stage plate 125. In this assembled state, compartment 170 of specimen plate holder 122 is aligned with opening 142 of stage plate 125. Although not required, specimen plate holder 122 can be secured to stage plate 125 using fasteners or by welding, adhesive or other conventional techniques. It is appreciated that specimen plate holder 122 is only one example of a manner of removably holding a specimen plate on stage plate 125 and that other configurations can also be used. For example, in some embodiments stage plate 125 and specimen plate holder 122 can be integrally formed from a single piece of material. In other embodiments, specimen plate holder 122 can be omitted and specimen plate 106 can be received directly within opening 142 on stage plate 125. In these embodiments, one or more arms or other securing mechanism can be used to secure specimen plate 10 directly to stage plate 125. Other configurations are also possible.

Once stage 118 is assembled, specimen plate 106 having biological material within the wells 115 can be inserted into specimen plate holder 122 while stage assembly 114 is in the retracted position, discussed above. As shown in the depicted embodiment, the specimen plate 106 seats against lip 172 of specimen plate holder 122 so as to be disposed within or above the compartment 170. Once the specimen plate 106 is positioned within stage 118, stage assembly 114 can then be placed in the retracted position, discussed above.

Figure 5:
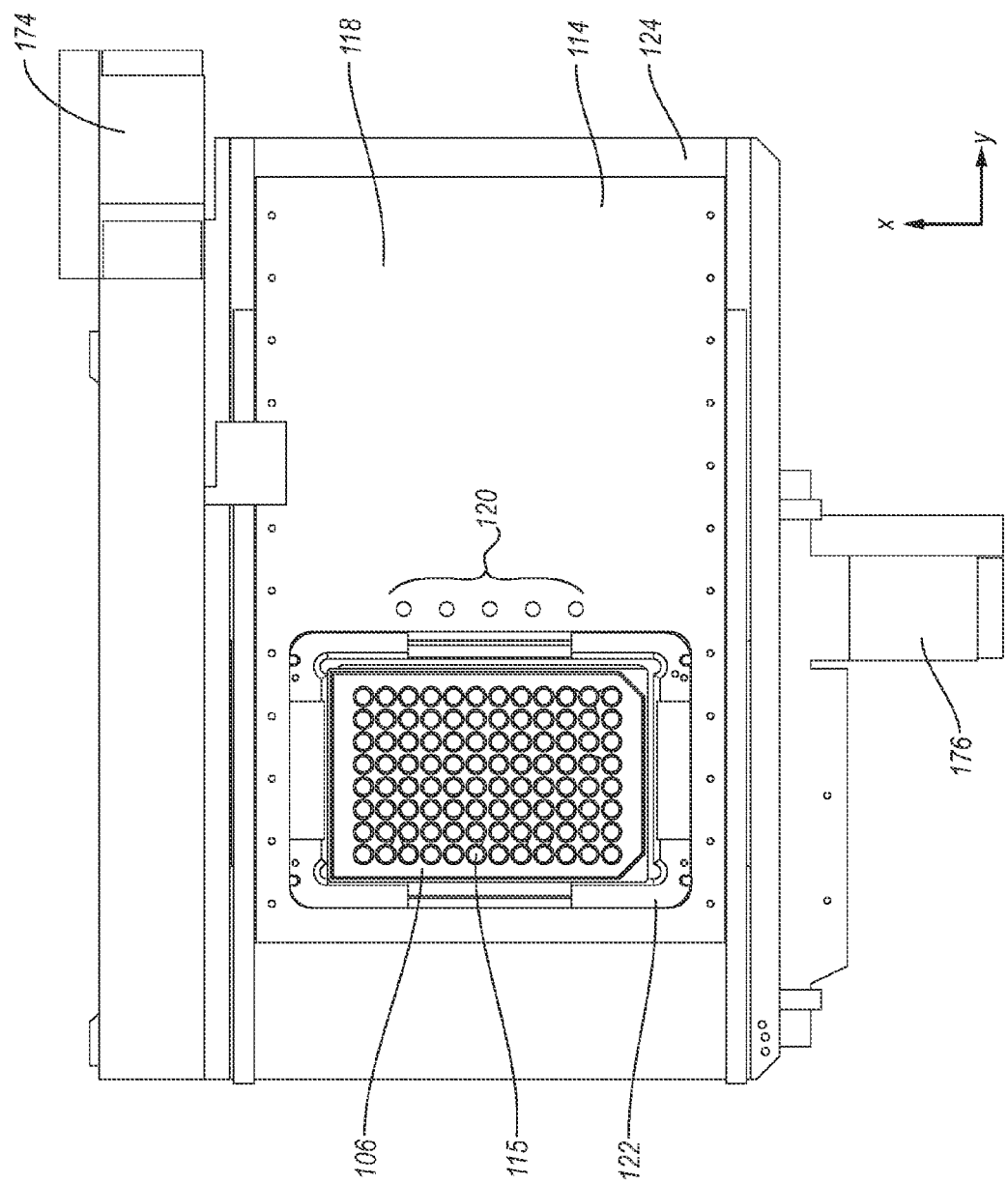
FIG. 5 is a top view of the stage assembly and specimen plate shown in FIG. 3 disposed on a stage moving assembly having motors used to move the stage assembly.

Turning to FIG. 5, a stage moving assembly 124 is used to move the stage 118 with respect to the microscope. Stage moving assembly 124 is adapted to receive stage 118 and includes two conventional motors 174 and 176 that move stage 118 in the y and x directions, respectively. As discussed below, motors 174 and 176 or their equivalents are also further used in the present invention to move the stage 118 with respect to the microscope to positions in which the calibration sample bays 120 are aligned with the objective of the microscope. Moving a commercial stage plate in the x and y directions so that wells of a specimen plate are aligned with an objective of a microscope is known in the art and any method of doing so can be used with the present invention. Many conventional stage assemblies can be used as stage moving assembly 124. For example, the stage moving assembly used in the ArrayScan HCS Reader manufactured by Thermo Scientific Cellomics can be used in embodiments of the current invention.

Figure 6:
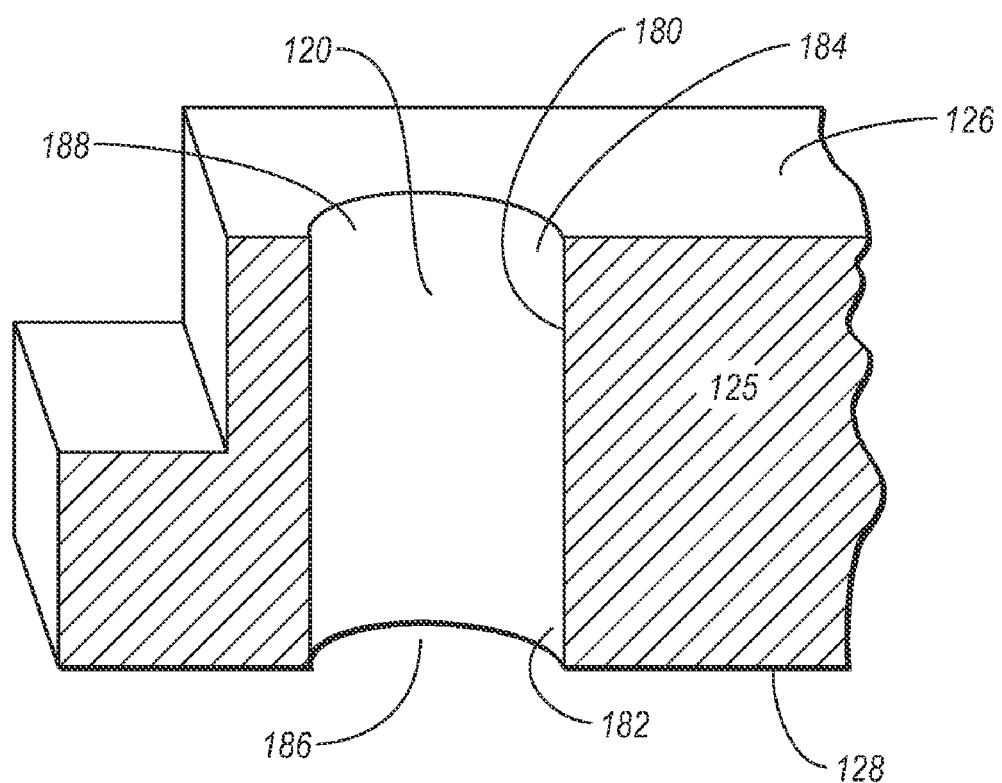
FIG. 6 is a cross sectional side view of a portion of the stage plate shown in FIG. 3 with a calibration sample bay formed therein.

Turning to FIG. 6, calibration sample bay 120 is bounded by an encircling sidewall 180 extending into stage plate 125 from bottom surface 128. Sidewall 180 extends substantially normal to bottom surface 128. Sidewall 180 can be smooth, rough, threaded, or incorporate other features configured to secure calibration samples therein. In the depicted embodiment, calibration sample bay 120 is generally cylindrically shaped and extends all the way through stage plate 125 from a first end 182 at bottom surface 128 to a second end 184 at top surface 126. As a result, calibration sample bay 120 has an open mouth 186 at bottom surface 128 and an open mouth 188 at top surface 126. As discussed below, in other embodiments, calibration sample bay 120 may not extend through top surface 126 and may incorporate various features within sidewall 180.

Figure 7A:
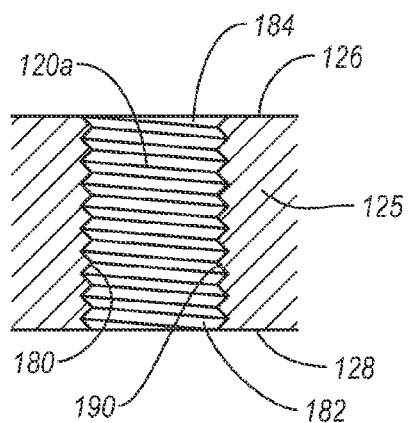
FIGS. 7A-7C are various embodiments of calibration sample bays.
Figure 7B:
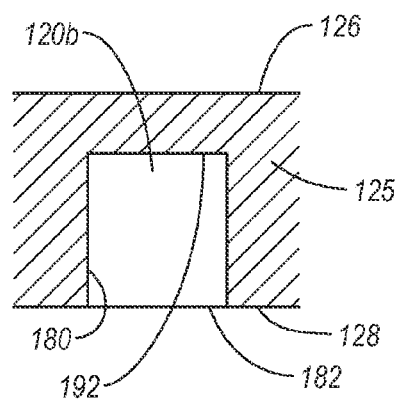
Figure 7C:
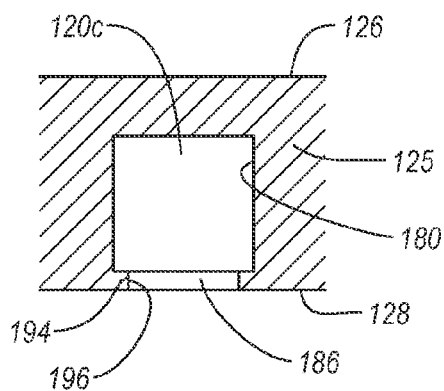

For example, FIGS. 7A-7C depict various embodiments of calibration sample bays 120 according to the present invention. FIG. 7A depicts a calibration sample bay 120a in which sidewall 180 incorporates one or more helical threads 190 therein that can be used to receive a matching threaded calibration sample. Although depicted as extending all the way along the entire length of sidewall 180 between first end 182 and second end 184, it is appreciated that threads 190 can instead extend along only a partial length of sidewall 180.

FIG. 7B depicts a calibration sample bay 120b that only extends partially through stage plate 125. That is, sidewall 180 extends from first end 182 to a floor 192 disposed within stage plate 125 so as to form a closed cylinder. As a result, calibration sample bay 120b is further bounded by floor 192. In the depicted embodiment, floor 192 is substantially planar and parallel to bottom surface 128, although this is not necessary.

FIG. 7C depicts a calibration sample bay 120c in which an annular lip 194 extends inward from sidewall 180 at mouth 186 to an inner surface 196. As a result, the diameter of inner surface 196 is less than the diameter of sidewall 180. This embodiment may be advantageous for receiving a calibration sample using a press-fit type of connection.

FIGS. 7A-7C are only examples of types of calibration sample bays 120 that can be used with the present invention. It is appreciated that many of the features shown in FIGS. 7A-7C can be mixed and matched with each other or with other embodiments of calibration sample bays 120 discussed herein. For example, the threads 190 shown in calibration sample bay 120a can be incorporate into a calibration sample bay that only extends partially through stage plate 125, such as calibration sample bay 120b. As another example, the annular lip 194 shown in calibration sample bay 120c can be incorporated into a calibration sample bay that extends completely through stage plate 125. Other combinations are also possible. It is also appreciated that other configurations can be used. For example, instead of having a substantially cylindrical cross section, calibration sample bay can have a rectangular, polygonal, or irregular cross section. Also, other securing structures can be incorporated with calibration sample bays 120. For example, structures allowing for bayonet style connection, adhesive attachment, screws, pins, set screws, etc. can also be used.

Calibration sample bay 120 can vary in size. In some embodiments the diameter of calibration sample bay 120 is about the same diameter as wells 115 in specimen plate 106. In other embodiments, the diameter of calibration sample bay 120 is larger or smaller then wells 115. For example, calibration sample bay 120 can have a diameter ranging from about 5 mm to about 20 mm, with about 7 mm to about 12 mm being common. Other diameters can also be used. Furthermore, calibration sample bay 120 can have a cross section that is circular, oval, polygonal, irregular, or any other shape.

As noted above, the stage can include one or more calibration sample bays. For example, in the embodiment depicted in FIG. 3, a single calibration sample bay 120 is formed within stage 118, whereas five sample bays 120 are incorporated in the embodiment depicted in FIG. 5. In other embodiments, two, three, four or more calibration sample bays are used. In still other embodiments, at least ten calibration sample bays are used with at least six calibration sample bays being common.

Figure 3A:
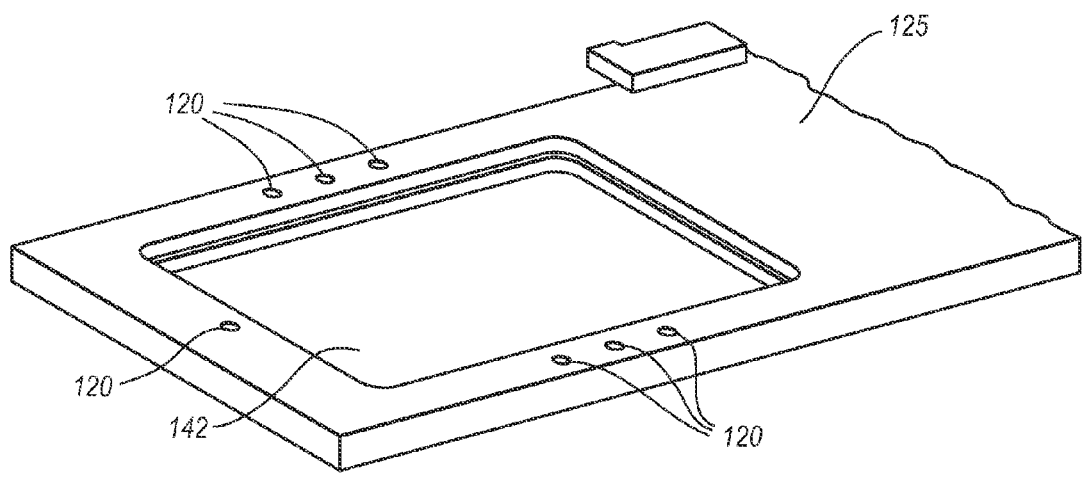
FIG. 3A is an exploded perspective view of a portion of the stage plate shown in FIG. 3 with the calibration sample bays being formed in alternative positions.

Irrespective of the number included, the calibration sample bays 120 are positioned in a location spaced apart from opening 142, as shown in the depicted embodiments. While the calibration sample bays are generally depicted herein as being distal to opening 142, such as in FIG. 3, this is not required. Alternatively, calibration sample bays 120 can be positioned proximally from opening 142 or on either side laterally from opening 142 or any combination thereof For example, in FIG. 3A, calibration sample bays 120 are positioned both proximally and laterally from opening 142. The limiting factor in the positioning of the calibration sample bays 120 is that the objective of the microscope must be able to be moved to a position aligned with the sample bays 120 so that the objective can image the calibration samples held within the calibration sample bays 120 (see, e.g., the position of objective 109 in FIG. 15).

When incorporating multiple calibration sample bays, the bays can be positioned in rows and/or columns on the stage, if desired. For example, in the embodiment depicted in FIG. 2, stage 118 includes a total of twelve calibration sample bays 120 arranged in two rows and six columns. Alternatively, all of the calibration sample bays 120 can be arranged in a single row if desired (see, e.g., FIG. 5). Also, if desired, the columns can be arranged so as to be aligned with one or more columns of wells included in the specimen plate. Other arrangements are also possible.

In embodiments having more than one calibration sample bay, each calibration sample bay can be the same or different size than the other calibration sample bays. Similarly, calibration sample bays on a single stage can all be of the same type, or be of different types. For example, one calibration sample bay may be threaded while another may incorporate a press fit or bayonet type connection. Still others may be configured for adhesive connection. Furthermore, calibration sample bays are typically formed in stage plate 125, as shown in FIG. 6, but can also be formed completely or at least partially within specimen plate holder 122 (see, e.g., FIG. 15).

As noted above, the calibration sample bays are configured to receive calibration samples. Calibration samples are defined herein to mean anything that can be inserted into the calibration sample bays and used to help calibrate the imaging system. The calibration samples typically include a fluorescent material, but that is not required. The imaging system can be calibrated by determining various system properties and adjusting the imaging system if needed based on the determined properties. Examples of imaging system properties that can be calibrated using calibration samples include optics and control properties. Examples of the optics properties include intensity, flatness of field, distortion, contrast, and resolution of the imaging system. Examples of the control properties include focus and positioning of the objective, such as vertical and horizontal offsets. Of course, the properties identified above are only exemplary and other properties can also be calibrated, as is known in the art.

The calibration samples can be categorized into at least six broad categories: images or printed matter, solid compositions, masks, liquids, particulates, and active samples. Other types of categories may also be used. In addition, the calibration samples can be comprised of various types of materials. A list of exemplary types of samples that can be used with the present invention is given in Tables 1-3, below. Table 1 lists exemplary uses for each sample type, Table 2 shows which category or categories can be associated with each particular sample type, and Table 3 lists exemplary materials that can be associated with each particular sample type.

TABLE 1

| Sample Type | Uses |
| --- | --- |
| OCS Fluorescence Sample | Intensity and Flatness of Field |
| OptiTracker Sample | Flatness of Field |
| Microparticles, Nanoparticles | Intensity calibration, distortion, resolution over field of view |
| Beads | Intensity calibration, distortion, resolution over field of view |
| LED (Active) | Diagnose failures of emission filter wheel |
| Impregnated Plastic For flat field | Flatness of Field |
| 1951 USAF Contrast Resolution Target | Paper targets for determining resolution of a system at different contrast levels. Determines limiting resolutions for a specific application. Allows a qualitative comparison of optics, most notably, lenses. Allows performance comparison for low contrast applications. |
| 1951 USAF Glass Slide Resolution Targets, NBS 1963A Resolution Target, UV Fused Silica and Fluorescent USAF 1951 Resolution Targets | Positive and Negative resolution samples. Used for quality control of magnification settings. Ideal for collimating optics and illuminations calibration |
| 1951 USAF Photographic Paper Resolution Targets | Evaluate resolution as a function of field and contrast. Similar to USAF contrast Resolution target. |
| Clear Optical Path USAF Target | Eliminates chromatic and absorption issues evaluating resolution of X-Ray, deep UV, Thermal, and Far-IR systems. Ideal for transmitted light imaging. |

TABLE 1-continued

| Sample Type | Uses |
|---|---|
| Color Scanner Test Target | Evaluates resolution and color density for color systems |
| DOF 5-15 Depth of Field Target | Angled target plane allows direct measurement of system depth of field. Eliminates calculations and estimations. Used to determine "acceptable image" criteria for a system. |
| Dot and Square Calibration Target, Concentric Square Target, Multi-Function High Magnification Calibration Targets | High contrast targets, positive and negative, used for detecting spatial aberrations; including distortion and blooming |
| EIA GrayScale Pattern Slide, Large Grayscale Target | Permanent density sample for light transmission. Ultra precise halftone pattern |
| EO Machine Vision Stage Micrometers, Image Analysis Micrometer, Multi-Grid Standard Stage Micrometer | Ensures accuracy of image measurements and overall scaling. 1D or 2D depending on micrometer type. |
| EO Telecentricity Target | Used to determine degree of telecentricity (perspective error). Used to determine imaging systems maximum accuracy and compare performance of optics. |
| Fixed Frequency Grid Distortion Targets, Variable Frequency Targets, Multi-Frequency Grid Distortion Targets | Used to measure and record precise distortion characteristics of an optical train. Ideal for "undoing" distortion in an image. Could be fixed or variable frequency dot sizes. Should be tailored for specific resolution ranges. Variable frequency targets allow for parfocal testing. |
| Gretag Macbeth ® Color Checker ® | Used for testing color balance. Allows calibration of system for luminous reflectance. |
| IEEE Target, Kodak Imaging Chart | Full field resolution calibration. Enables checking of linearity, aspect ration, shading, and interlacing of an imaging system. Could be used to reduce system to system variability. |
| Line Grid Target | Test and correction of distortion, perspective error, and field of view. |
| Precision Ronchi Ruling Glass Slides | Evaluate resolution, field distortion, and parfocal stability. |
| Reflective Scanner Test Target | Measurement of reflected light resolution. |
| Resolving Power Chart | Testing for chromatic aberrations of color systems as well as astigmatism. |
| Sinusoidal Targets | Determining and calibrating contrast levels. Specifically for MTF testing. |
| Star Target | Determining focus errors and Astigmatism, and other aberrations. |
| White Balance Reflectance Targets | Calibration of back light illuminations. Allows correlation of input vs. output measurements, specifically "white balance". Assists in color balancing. |
| ISO-14524 Reflective Camera Contrast Chart | For determining a systems functional range of optical density. |
| Star Target Arrays | Allows for determining precision, amplitude, and locations of focus errors, astigmatism. Detection of aberrations at various field points. |
| Micro Line and Dot Standard Stage Micrometer | Calculate pixel dithering |
| Dual Axis Linear Scale Stage Micrometer | Allows calibration of both X and Y camera aspect values without rotation. |
| Opal Glass Concentric Circles Reticle Target | Calibration of laser spot size, focus, and bore sighting. |
| Opal Glass Index Grid Reticle Target | Reticle target, combined with bead sample, would aids in particle counting, blob analysis, and general morphology verification. |
| ISO-21550 Dynamic Range Film | Determine optical density range for transmitted light applications. |

TABLE 2

| Sample Type | images or printed matter | solid compositions | masks | liquids | particulates | active samples |
|---|---|---|---|---|---|---|
| OCS Fluorescence Sample | ✓ | ✓ | | | | |
| OptiTracker Sample | | | | ✓ | | |
| Microparticles, Nanoparticles | | | | | ✓ | |
| Beads | | | | | ✓ | |
| LED (Active) | | | | | | ✓ |
| Impregnated Plastic For flat field | ✓ | ✓ | | | | |
| 1951 USAF Contrast Resolution Target | ✓ | | | | | |
| 1951 USAF Glass Slide Resolution Targets, NBS 1963A Resolution Target, UV Fused Silica and Fluorescent USAF 1951 Resolution Targets | | ✓ | ✓ | | | |

TABLE 2-continued

| Sample Type | images or printed matter | solid compositions | masks | liquids | particulates | active samples |
|---|---|---|---|---|---|---|
| 1951 USAF Photographic Paper Resolution Targets | ✓ | | | | | |
| Clear Optical Path USAF Target | | ✓ | ✓ | ✓ | | |
| Color Scanner Test Target | | ✓ | | | | |
| DOF 5-15 Depth of Field Target | | ✓ | ✓ | | | |
| Dot and Square Calibration Target, Concentric Square Target, Multi-Function High Magnification Calibration Targets | ✓ | | ✓ | ✓ | | |
| EIA GrayScale Pattern Slide, Large Grayscale Target | ✓ | | ✓ | ✓ | | |
| EO Machine Vision Stage Micrometers, Image Analysis Micrometer, Multi-Grid Standard Stage Micrometer | | | ✓ | ✓ | | |
| EO Telecentricity Target | | | ✓ | ✓ | | |
| Fixed Frequency Grid Distortion Targets, Variable Frequency Targets, Multi-Frequency Grid Distortion Targets | | | ✓ | ✓ | | |
| Gretag Macbeth ® Color Checker ® | | ✓ | | | | |
| IEEE Target, Kodak Imaging Chart | | ✓ | | | | |
| Line Grid Target | | | ✓ | ✓ | | |
| Precision Ronchi Ruling Glass Slides | | | ✓ | ✓ | | |
| Reflective Scanner Test Target | ✓ | | ✓ | ✓ | | |
| Resolving Power Chart | | ✓ | | | | |
| Sinusoidal Targets | | ✓ | ✓ | | | |
| Star Target | ✓ | | ✓ | ✓ | | |
| White Balance Reflectance Targets | | | ✓ | | | |
| ISO-14524 Reflective Camera Contrast Chart | ✓ | | ✓ | | | |
| Star Target Arrays | ✓ | | ✓ | | | |
| Micro Line and Dot Standard Stage Micrometer | | | ✓ | ✓ | | |
| Dual Axis Linear Scale Stage Micrometer | | | ✓ | ✓ | | |
| Opal Glass Concentric Circles Reticle Target | | | ✓ | ✓ | | |
| Opal Glass Index Grid Reticle Target | | | ✓ | ✓ | | |
| ISO-21550 Dynamic Range Film | ✓ | | ✓ | | | |

TABLE 3

| Sample Type | Photo Bleaching | Fluorescent | Glass | Heavy Metals | Dye | Paper/Mylar | Chromium | Plastic | Ink | Film |
|---|---|---|---|---|---|---|---|---|---|---|
| OCS Fluorescence Sample | | ✓ | ✓ | ✓ | | | | | | |
| OptiTracker Sample | ✓ | ✓ | ✓ | ✓ | ✓ | | | | | |
| Microparticles, Nanoparticles | | ✓ | ✓ | ✓ | | | | | | |
| Beads | ✓ | ✓ | | | ✓ | | | | | |
| LED (Active) | | ✓ | | | | | | | | |
| Impregnated Plastic For flat field | | ✓ | | ✓ | | | | ✓ | | |
| 1951 USAF Contrast Resolution Target | | | | | | ✓ | | | ✓ | ✓ |
| 1951 USAF Glass Slide Resolution Targets, NBS 1963A Resolution Target, UV Fused Silica and Fluorescent USAF 1951 Resolution Targets | | ✓ | ✓ | | | | ✓ | | | ✓ |
| 1951 USAF Photographic Paper Resolution Targets | | | | | | ✓ | | | ✓ | |
| Clear Optical Path USAF Target | | | ✓ | | | ✓ | | ✓ | | |
| Color Scanner Test Target | | | | | | ✓ | | | ✓ | |
| DOF 5-15 Depth of Field Target | | | ✓ | | | | | ✓ | | |
| Dot and Square Calibration Target, Concentric Square Target, Multi-Function High Magnification Calibration Targets | | | ✓ | | | | | ✓ | | |
| EIA GrayScale Pattern Slide, Large Grayscale Target | | | ✓ | | | | | ✓ | | |
| EO Machine Vision Stage Micrometers, Image Analysis Micrometer, Multi-Grid Standard Stage Micrometer | | | ✓ | | | | | ✓ | | |
| EO Telecentricity Target | | | ✓ | | | | ✓ | | ✓ | ✓ |
| Fixed Frequency Grid Distortion Targets, Variable Frequency Targets, Multi-Frequency Grid Distortion Targets | | | ✓ | | | | ✓ | | ✓ | ✓ |
| Gretag Macbeth ® Color Checker ® | | | | | | ✓ | | | ✓ | |
| IEEE Target, Kodak Imaging Chart | | | | | | ✓ | | | ✓ | |
| Line Grid Target | | | ✓ | ✓ | | ✓ | | ✓ | ✓ | ✓ |
| Precision Ronchi Ruling Glass Slides | | | ✓ | | | | | ✓ | | |
| Reflective Scanner Test Target | | | ✓ | | | | | ✓ | | |
| Resolving Power Chart | | | ✓ | | | ✓ | | ✓ | | |
| Sinusoidal Targets | | | ✓ | | | ✓ | | | ✓ | ✓ |
| Star Target | | | ✓ | | | ✓ | | | ✓ | ✓ |
| White Balance Reflectance Targets | | | | | | ✓ | | | | |
| ISO-14524 Reflective Camera Contrast Chart | | | ✓ | | | | | ✓ | | |

TABLE 3-continued

| Sample Type | Photo Bleaching | Fluorescent | Glass | Heavy Metals | Dye | Paper/Mylar | Chromium | Plastic | Ink | Film |
|---|---|---|---|---|---|---|---|---|---|---|
| Star Target Arrays | | ✓ | | | | | ✓ | | | ✓ |
| Micro Line and Dot Standard Stage Micrometer | | ✓ | | | | | ✓ | | | ✓ |
| Dual Axis Linear Scale Stage Micrometer | | ✓ | | | | | ✓ | | | |
| Opal Glass Concentric Circles Reticle Target | | ✓ | | | | | ✓ | | | ✓ |
| Opal Glass Index Grid Reticle Target | | ✓ | | | | | ✓ | | | ✓ |
| ISO-21550 Dynamic Range Film | | ✓ | | | | | | | | ✓ |

Figure 8:
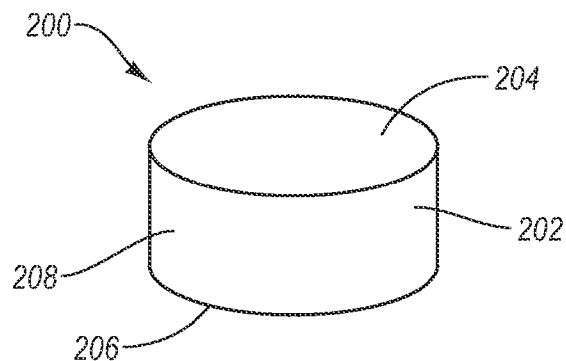
FIG. 8 is a perspective view of one embodiment of a calibration sample.

One example of a calibration sample 200 that can be used with the present invention is shown in FIG. 8. Calibration sample 200 comprises a glass plug 202 that is coated or otherwise treated with a fluorescent material. Plug 202 comprises a top surface 204 and an opposing bottom surface 206 having an encircling sidewall 208 extending therebetween. The top and/or bottom surfaces 204 and 206 can be frosted or matted to provide a more even distribution of viewed fluorescence.

In the depicted embodiment, top and bottom surfaces 204 and 206 are generally circular, planar, and parallel to each other so that plug 202 generally forms a cylinder. Other shapes are also possible. For example, one or both of the surfaces of plug 202 may have a rounded concave or convex shape instead of being planar. Furthermore, instead of being generally circular, top and bottom surfaces 204 and 206 can instead be oval, rectangular, polygonal, irregular, or any other shape. Other variations can also be used, as long as calibration sample 200 can fit within calibration sample bay 120. Also, instead of glass, plug 202 can be comprised of polymeric plastics, metal, or any other material known in the art.

To form calibration sample 200, a fluorescent material is coated onto all or part of plug 202 or is impregnated into plug 202, as is known in the art. For example, the fluorescent material can be sintered onto one or both surfaces 204, 206 of plug 202. The fluorescent material is typically comprised of an ionized heavy metal, such as Nd3+, Sm3+, Eu3+, U6+, Ce3+. Other fluorescent materials can alternatively be used, such as, e.g., mirrored glass, fluorescently stained cells, and colored beads.

Calibration sample 200 is sized and shaped so as to fit within calibration sample 200. As such, calibration sample can have a diameter ranging from about 2 mm to about 18 mm, with about 3 mm to about 10 mm being common and about 6 mm to about 10 mm being more common. Other diameters can also be used.

Figure 9A:
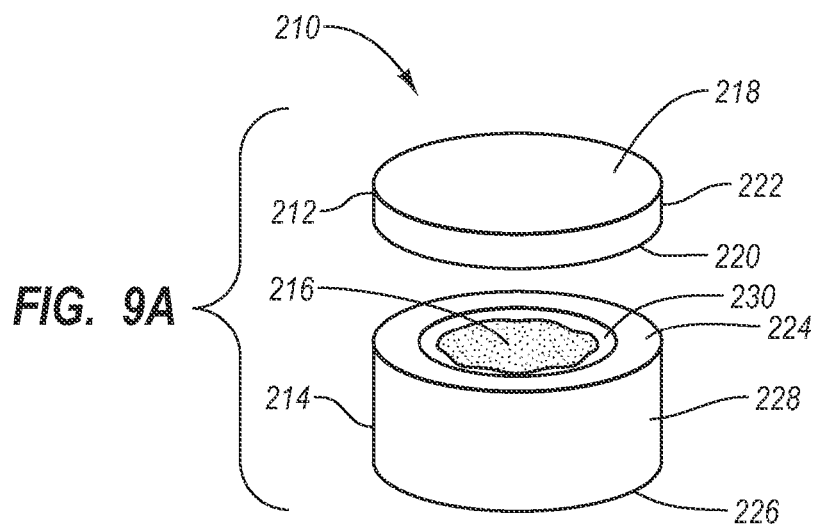
FIG. 9A is a perspective view of another embodiment of a calibration sample in an unassembled state.
Figure 9B:
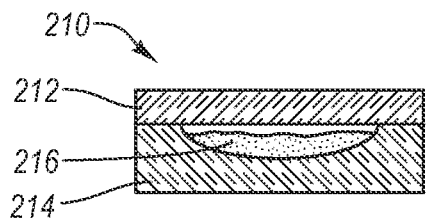
FIG. 9B is a cross sectional side view of the calibration sample shown in FIG. 9A in an assembled state.

Another example of a calibration sample 210 that can be used with the present invention is shown in FIGS. 9A and 9B. Calibration sample 210 incorporates a fluorescent material in liquid form in an integrated package. Integrated calibration sample 210 comprises a top disk 212 disposed on a bottom disk 214, with a compartment being formed therebetween, a fluorescent sample 216 being disposed within the compartment.

Top disk 212 comprises a top surface 218 and an opposing bottom surface 220 having an encircling sidewall 222 extending therebetween. Top and bottom surfaces 218 and 220 are generally circular, planar, and parallel to each other so that top disk 212 generally forms a cylinder.

Similar to top disk 212, bottom disk 214 also comprises a top surface 224 and an opposing bottom surface 226 having an encircling sidewall 228 extending therebetween. Top and bottom surfaces 224 and 226 are also generally circular, with a diameter that is substantially the same as that of top disk 212. While bottom surface 226 is generally planar, at least a portion 230 of top surface 224 is substantially concave or has a depression so as to be able to receive the fluorescent sample 216 in liquid form.

Top and bottom disks 212 and 214 are typically comprised of glass. Other materials, such as those listed for plug 202, can also be used. Any or all of the top and bottom surfaces 218, 220, 224, 226 of top and bottom disks 212, 214 can be frosted or matted to provide a more even distribution of viewed fluorescence.

To assemble integrated calibration sample 210, the fluorescent sample 216 is first positioned within the concave portion 230 of the top surface 224 of bottom disk 214. Then the top disk 212 is positioned on bottom disk 214 such that bottom surface 220 of top disk 218 contacts top surface 224 of bottom disk 214 and sidewalls 222 and 228 are vertically aligned, as shown in FIG. 9B. Once positioned thusly, top disk 212 and bottom disk 214 are sealed with epoxy or other type of adhesive. Once assembled, integrated calibration sample 210 typically has the same general outer size and shape as calibration sample 200 and can generally be interchanged with calibration sample 200. That is, in most, if not all, of the embodiments described herein that include calibration sample 200, integrated calibration sample 210 can replace calibration sample 200 and be used therein.

Although the discussion of integrated calibration sample 210 has been centered on a liquid sample 216 being disposed within portion 230, it is appreciated that a solid, powder, beads, or other type of material can alternatively be used.

Furthermore, similar to calibration sample 200, the top and/or bottom surfaces 218, 226 of integrated calibration sample 210 may have rounded concave or convex shapes instead of being planar, and instead of being generally circular, top and bottom disks 212 and 214 can instead be oval, rectangular, polygonal, irregular, or any other shape.

Calibration samples 200 and 210 can incorporate fluorescent materials that photo-bleach over time, or fluorescent or other materials that do not photo-bleach over time. Non photo-bleaching samples can be used to measure the intensity of the imaging light in various channels or to determine the correct x, y and z offsets (i.e., horizontal and vertical offsets) during setup or usage of the stage. Photo-bleaching samples can be used to mimic and test the dyes used or to compensate for variability in the light source from imaging system to imaging system, thereby allowing normalization of results between readers. It is also possible to quantify the light intensity (energy) that is exiting the sample by measuring the rate of photo-bleaching if the decay curve of the sample material is known. Other uses are also possible for each type of sample. Exemplary types of substrates and targets that can be used with the different types of materials are shown in Table 4 below.

TABLE 4

| Material Type | Substrates | Targets |
|---|---|---|
| Photo Bleaching | Plastic (acrylic, lexan) | Dyed Beads (Polystyrene) |
| | Glass (silica, soda lime, opal) | Fixed Biology (Prepared Cells) |
| | | Dye Solution (Liquid) |
| Non-Photo Bleaching, Non-Fluorescent (Transmitted or Reflected Light) | Paper | Laser Cutout |
| | Plastic (acrylic, lexan) | Chromium Oxide (black masking) |
| | Photographic Film (polyester, nitrocellulose, cellulose acetate) | Chromium |
| | Mylar | Photographic Film |
| | Ceramic | Ink/Paint |
| | Glass (silica, soda lime, opal) | |
| | Nickel (cutout shapes) | |
| Non-Photo Bleaching, Fluorescent (Emitted Light) | Plastic (acrylic, lexan) | Conventional Zinc/Cadmium |
| | Glass (silica, soda lime, opal) | Ionized Heavy Metals (nano/micro particulate) |
| Active (Powered) Sample | LED | |

Calibration samples 200 can be inserted and secured within the calibration sample bays 120 in various manners, depending on the type of calibration bays 120 being used. In some embodiments, the calibration sample 200 is placed directly into the calibration bay 120, while in other embodiments, the calibration sample 200 is positioned within a calibration insert housing so as to form a calibration sample insert, which is then secured within the calibration sample bay, as discussed below.

Figure 10:
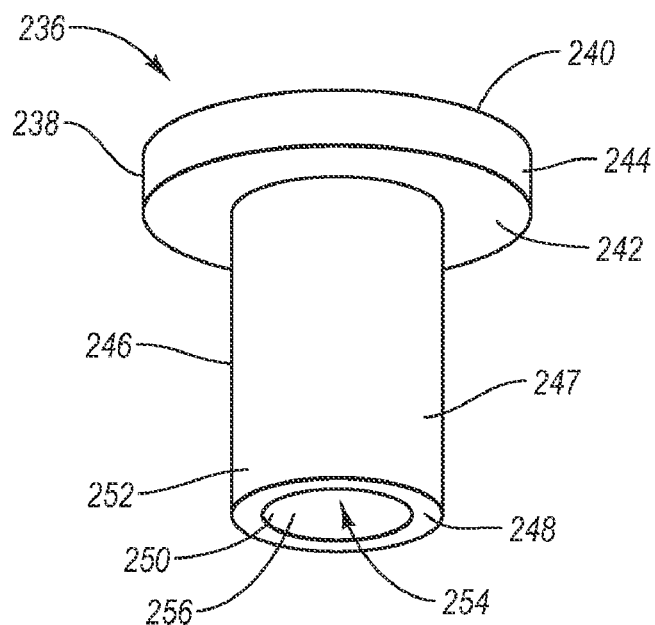
FIG. 10 is a perspective view of one embodiment of a calibration insert housing.

One example of a calibration insert housing 236 that can be used with the present invention is shown in FIG. 10. Calibration insert housing 236 comprises a head 238 having a top surface 240 and an opposing bottom surface 242 with an encircling side surface 244 extending therebetween. Head 238 can be substantially cylindrical, as depicted, or can be hexagonally shaped, so as to be mateable with a socket or other type of wrench. Other shapes can also be used. Alternatively, head 238 can have one or more slots 245 (see FIG. 19) formed thereon so as to receive a blade of a screwdriver or the like.

A main body 246 projects substantially normally from the bottom surface 242 of head 238 to an end face 248 spaced apart from the bottom surface 242. Main body 246 comprises a sidewall 247 having an inner surface 250 and an opposing outer surface 252 forming an open ended hollow cylinder, the inner surface 250 and bottom surface 242 bounding a bore 254 having an open mouth 256. Outer surface 252 of sidewall 247 can be substantially smooth, as depicted, so as to be able to be press-fit into calibration sample bay 120. Alternatively, outer surface 252 can have a rough surface so as to provide a better frictioned grip within calibration sample bay 120, or can have one or more threads 258 (see FIG. 13) that mate with threads 190 (see FIG. 7A) formed within calibration sample bay 120. In some embodiments, outer surface 252 is formed or has structure attached to it so as to allow calibration insert housing to be secured within calibration sample bay 120 by bayonet style connection. Calibration insert housing 236 can be designed to allow other manners of connection as well, such as screw, pin, and set screw connections, as well as others.

Calibration insert housing 236 is typically made of anodized aluminum, but other materials can also be used. For example, calibration insert housing 236 can alternatively be made of a different type of metal, an alloy, a polymeric material, a plastic material, or other type of material.

Figure 11:
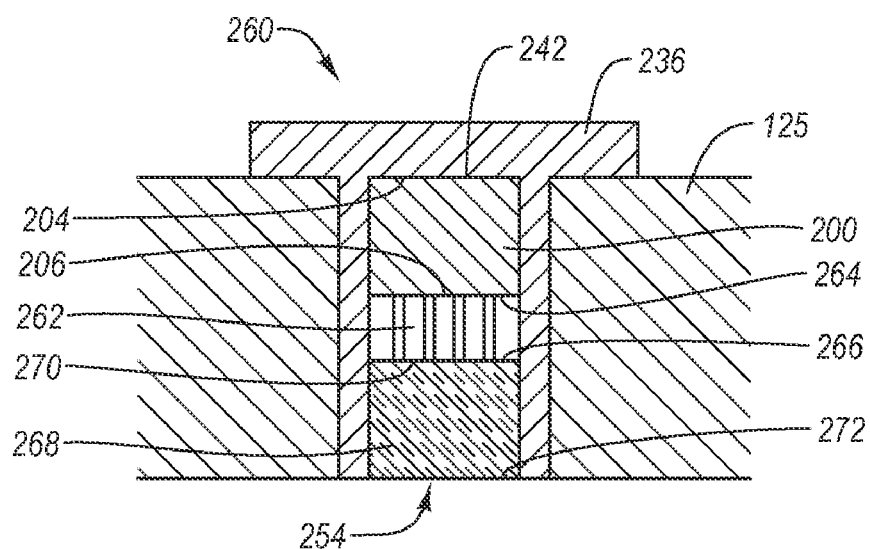
FIG. 11 is a cross sectional side view of one embodiment of a calibration insert positioned within a calibration sample bay.

A calibration sample insert is formed by positioning a calibration sample, along with other objects, within the calibration insert housing. For example, FIG. 11 depicts one embodiment of a calibration sample insert 260 used for calibrating the focus or positioning of the objective according to the present invention. Note that in FIG. 11, calibration sample insert 260 has been press fit into the stage plate 125 of the stage 118. A threaded connection, such as used by calibration sample insert 276 (see FIG. 13), or other type of connection can alternatively be used.

To assemble calibration sample insert 260, calibration sample 200 is inserted into bore 254 of calibration insert housing 236 so that top surface 204 of calibration sample 200 is adjacent to bottom surface 242 of calibration insert housing 236. Next, a grid 262 having a top surface 264 and an opposing bottom surface 266 is inserted into bore 254 so that top surface 264 is adjacent to bottom surface 206 of calibration sample 200. Finally, a protective layer 268 having a top surface 270 and an opposing bottom surface 272 is inserted into bore 254 so that top surface 270 is adjacent to bottom surface 266 of grid 262. Protective layer 268 is then epoxied, or otherwise secured to calibration insert housing 236 to complete the assembly of calibration sample insert 260. Applicant notes that although calibration sample 200 is used in the depicted embodiment, calibration sample 210 can alternatively be used.

Figure 12:
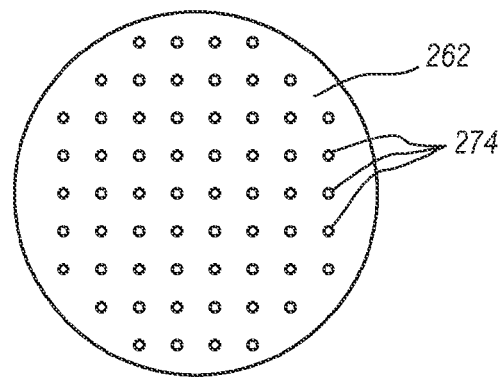
FIG. 12 is a top plan view of a grid used in the calibration insert shown in FIG. 11.

Turning to FIG. 12 in conjunction with FIG. 11, grid 262 comprises a thin light-blocking material having a plurality of spaced apart holes 274 formed therein. The holes 274 are generally evenly spaced apart from each other to allow the objective to calibrate its focus based on the holes 274. Each of holes 274 can have a diameter between about 5 microns and about 50 microns in diameter, with about 10 microns being common. Furthermore, holes 274 can all have the same diameter or can vary in size. Grid 262 can be comprised of any material that can block the fluorescent light emanating from calibration sample 200 without photoreacting with the light. For example, grid 262 can be comprised of a metal, an alloy, or certain plastics. Other materials can also be used.

The grid arrangement shown in FIGS. 11 and 12 can also be used for other types of calibration. For example, contrast between the light-blocking material and the light passing through the holes 274 can be used to determine the state of the optic filters or the light source and to thereby calibrate the system. When the pattern of FIG. 12 is viewed in the system it should provide a sharp contrast between the bright spots where the holes are and the dark regions where there are no holes. If there is a problem in the optical system, then one will get less bright circles and/or less contrast.

During use, the fluorescent material within calibration sample 200 fluoresces. However, grid 262 blocks the light that emanates from calibration sample 200 from passing therethrough, except for where holes 274 are located. When the objective is positioned below calibration sample insert 260, the small amount of light passing through the holes 274 allows the objective to be focused, either manually or automatically, using the holes 274 as the focusing objects.

As noted above, the fluorescent material used in the present invention can be photo-bleaching or non photo-bleaching. When using the calibration sample 200 or 210 to calibrate the focus or positioning of the objective, a non photo-bleaching fluorescent material is typically used. Because the fluorescent material is non photo-bleaching, the fluorescing properties remain constant for a long time. As a result, the calibration sample insert 260 containing the non photo-bleaching material can remain disposed within calibration sample bay 120 for a long time.

Figure 13:
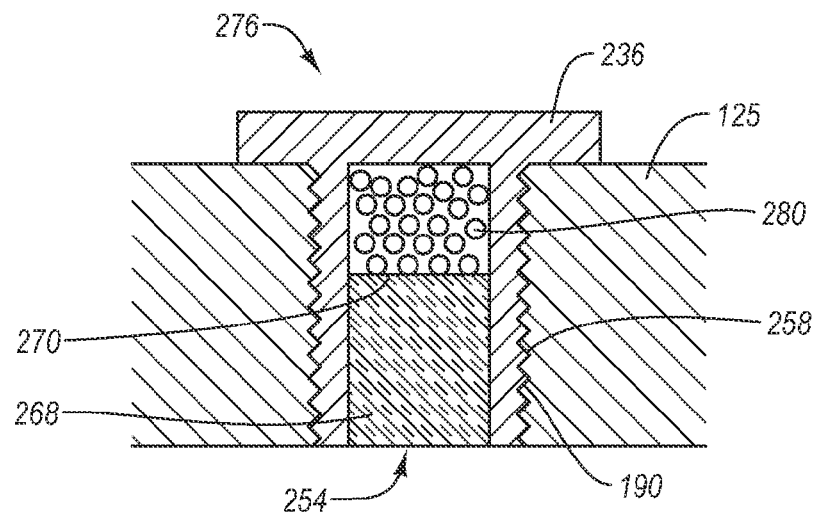
FIG. 13 is a cross sectional side view of another embodiment of a calibration insert positioned within a calibration sample bay.

FIG. 13 depicts an alternative embodiment of a calibration sample insert 276 that is used to calibrate optical or other system properties. Note that in FIG. 13, calibration sample insert 276 has been threaded into the stage plate 125 of the stage 118. A press fit connection, such as used by calibration sample insert 260, or other type of connection can alternatively be used. Calibration sample insert 276 is similar to calibration sample insert 260, except that grid 262 is omitted and calibration sample 200 is replaced with a different type of calibration sample, one or more fluorescent beads 280 of a predetermined color. Because of the omission of grid 262, the fluorescent light that emanates from beads 280 is not blocked, but passes through protective layer 268 and can be used in the calibration of other system properties, such as optical properties.

For example, because beads 280 are of a particular predetermined color, beads 280 fluoresce at a particular, narrow, wavelength. For example, whereas the calibration sample 200 may fluoresce broadly between, e.g., 375 nm to 550 nm, the beads 280 may only fluoresce narrowly between, e.g., 475 nm to 500 nm. Because of this, the color readings of the system can be tested and adjusted to match the color of the dyes or filters being used when performing HCS. Applicant notes that the values given above regarding the fluorescent wavelengths are exemplary only; any fluorescent wavelength range known in the art can be used. In these embodiments, a photo-bleaching material is typically used in beads 280 to account for optics changes that may take place in the imaging system over time. Furthermore, by using beads having a known diameter, distances and diameters determined by the imaging system can also be tested and adjusted.

In some embodiments, the user may have several different calibration sample inserts 276 containing different sets of beads 280 such that each calibration sample insert 276 fluoresces at different narrow wavelengths. A particular calibration sample insert 276 can be chosen and inserted into calibration sample bay 120 depending on the particular wavelength desired by the user. When a different wavelength is desired to be tested, the user can remove the original calibration sample insert 276 from the calibration sample bay 120 and replace it with a different calibration sample insert 276 accordingly. Alternatively, as discussed below, in imaging systems having multiple calibration sample bays 120, each calibration sample insert 276 can remain installed within the different calibration sample bays 120 and used when desired without requiring replacement of any of the calibration sample inserts 276. Furthermore, different types of calibration samples can be simultaneously disposed in the same imaging system. For example, in an imaging system containing at least two calibration sample bays 120, a calibration sample comprising a photo-bleaching fluorescent material can be installed in one of the calibration sample bays 120 and a second calibration sample comprising a non-photo-bleaching material can be installed in another calibration sample bay 120.

In alternative embodiments, instead of using beads 280, calibration sample insert 276 can use calibration sample 200 or 210 having a fluorescent material that also fluoresces in a narrow bandwidth, if desired. In these embodiments, a photo-bleaching material can be used. Of course, calibration sample 200 or 210 can alternatively have a fluorescent material that fluoresces in a wide bandwidth, if desired.

Figure 14:
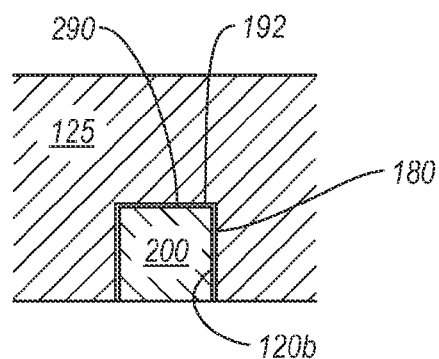
FIG. 14 is a cross sectional side view of a calibration sample bay with a calibration sample adhered therein.

As noted above, in some embodiments the calibration sample can be inserted directly into the calibration sample bay. In the simplest of these embodiments, the calibration sample is simply secured within a calibration bay having a closed end, (see, e.g., calibration bay 120b in FIG. 7B) by an adhesive or the like. For example, FIG. 14 depicts one such embodiment. In FIG. 14, calibration sample 200 is positioned within calibration sample bay 120b and secured therein by an adhesive 290. Adhesive 290 can adhere calibration sample 200 to the floor 192 of calibration sample bay 120b, as depicted, and/or to the sidewall 180. Adhesives that can be used include glues, epoxies, or the like. These embodiments may work well for calibration samples that are not intended to be replaced.

In an alternative embodiment, instead of or in conjunction with adhesive 290, calibration sample 200 can be secured within closed-ended calibration sample bay 120b by use of a mask plate, as discussed below.

Figure 15:
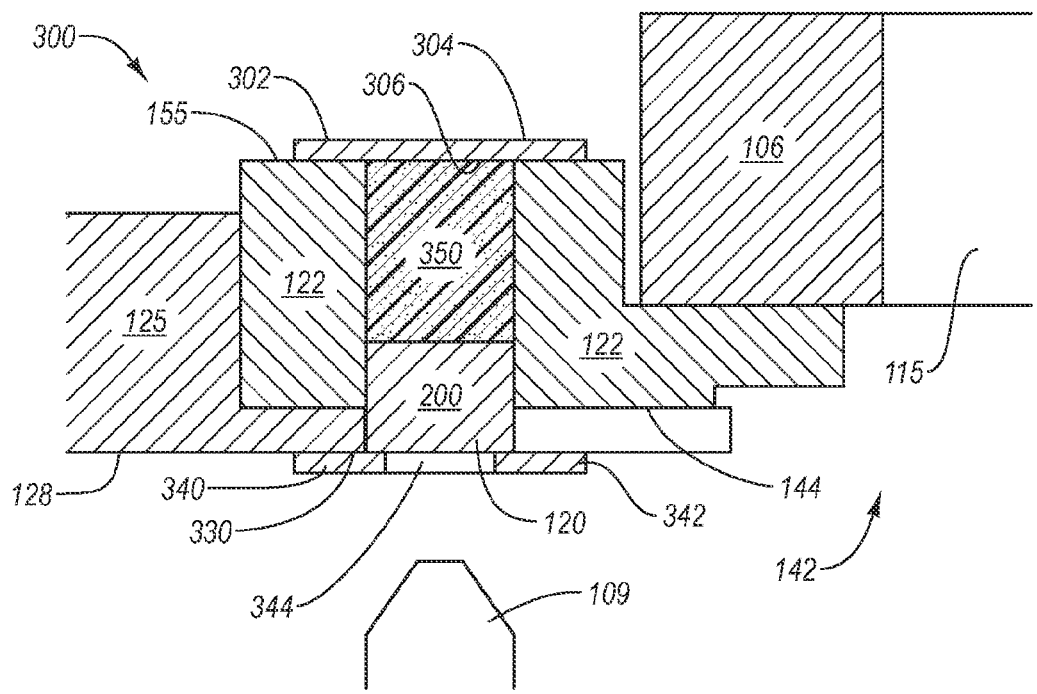
FIG. 15 is a cross sectional side view of a portion of an assembled stage assembly that incorporates a securing member and mask plate respectively disposed above and below the calibration sample bay.

In alternative embodiments, the calibration sample can be secured within the calibration sample bay by using a removable securing member. These embodiments work well when using multiple calibration sample bays and/or for calibration samples that are intended to be replaced from time to time. FIG. 15, which shows an embodiment in which the calibration sample bay 120 is partially formed on specimen plate holder 122, depicts an assembled stage assembly 300 that incorporates a securing member 302 disposed on the upper surface 155 of specimen plate holder 122 to help secure calibration sample 200 within calibration sample bay 120. In the depicted embodiment, calibration sample bay 120 is disposed so as to pass through both specimen plate holder 122 and shoulder 144 of stage plate 125. It is appreciated that calibration sample bay 120 used in stage assembly 300 can alternatively be formed entirely within stage plate 125, if desired.

Figure 16:
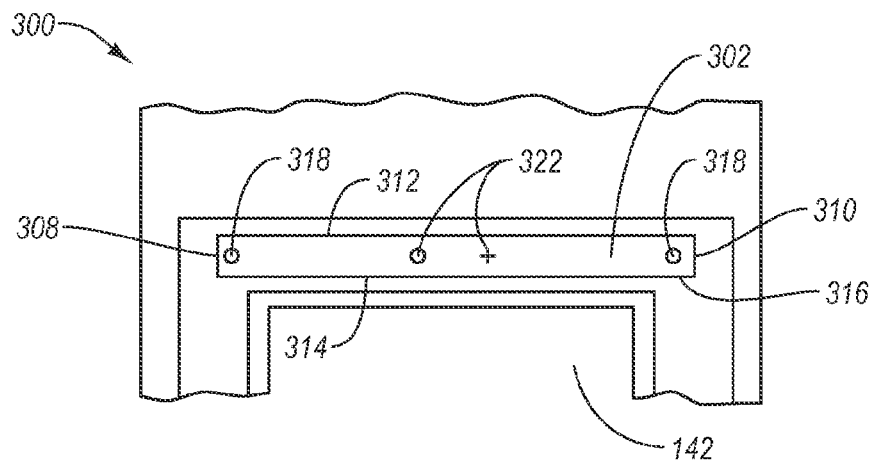
FIG. 16 is a top plan view of a portion of the assembled stage assembly shown in FIG. 15.

Turning to FIG. 16 in conjunction with FIG. 15, securing member 302 comprises a generally flat plate having a top surface 304 and an opposing bottom surface 306 extending between a first end 308 and a spaced apart second end 310 and between a first side 312 and an opposing second side 314. When secured to the top surface 155 of specimen plate holder 122, securing member 302 is positioned so as to cover calibration sample bays 120. Towards this end, securing member 302 has through holes 318 formed therein between top and bottom surfaces 304 and 306 at first and second ends 308 and 310 through which receiving screws 311 (see FIG. 17) can thread into mating threaded bores 320 (see FIG. 17) in specimen plate holder 122 or stage plate 125. Alternatively, securing member 302 can be secured to specimen plate holder 122 or stage plate 125 using a bayonet type of arrangement, adhesives, or other securing method known in the art. In some embodiments specimen plate holder 122 or stage plate 125 can have a channel formed on the top surface thereof that matches the shape of securing member 302. In those embodiments securing member 302 is prevented from moving by being disposed within the channel.

Furthermore, small registration holes or marks 322 can be formed on securing member 302, if desired. The registration holes or marks 322 are positioned directly above one or more of the calibration sample bays 120 when securing member 302 is secured to specimen plate holder 122 or stage plate 125. These registration holes or marks 322 can aid the user in positioning the stage assembly 300 so as to place the desired calibration sample bay 120 directly above the objective 109. The registration holes or marks 322 can pass completely through the securing member 302 or can be formed on the top surface 304 thereof.

Securing member 302 can be comprised of a thin metal, such as aluminum, or a polymeric material, or the like. Securing member 302 has a thickness that is typically between about 0.5 mm to about 4 mm, with about 1 mm to about 2 mm being common. Other thicknesses can also be used.

Returning to FIG. 15, a mask plate 330 can be positioned on the bottom surface 128 of stage plate 125 opposite the securing member 302. The mask plate 330 acts as a bottom securing member that in conjunction with securing member 302 effectively "sandwiches" and secures the calibration sample 200 within calibration sample bay 100.

Figure 17:
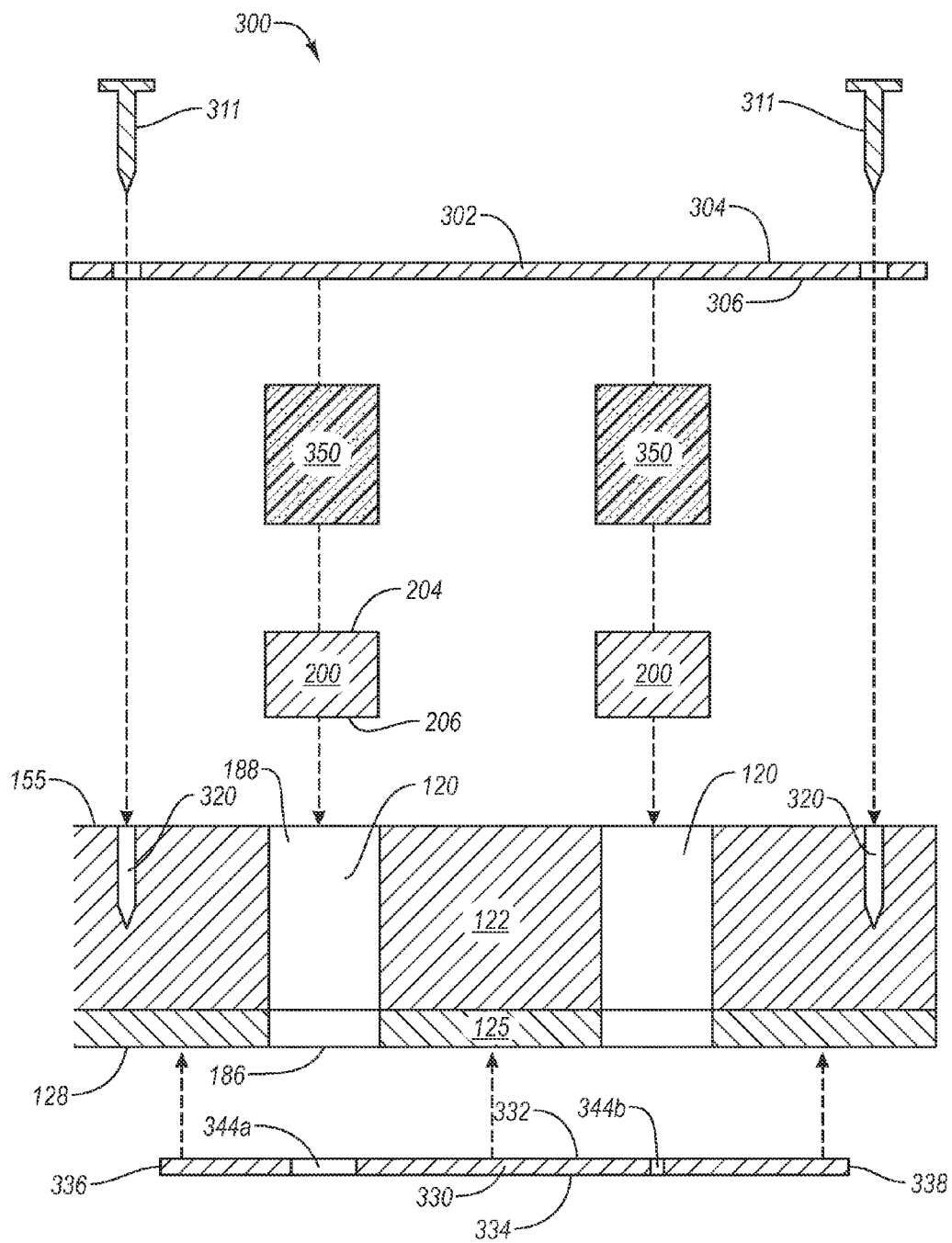
FIG. 17 is an exploded cross sectional front view of a portion of the stage assembly shown in FIGS. 15 and 16.

Turning to FIG. 17 in conjunction with FIG. 15, mask plate 330 comprises a generally flat plate having a top surface 332 and an opposing bottom surface 334 extending between a first end 336 and a spaced apart second end 338 and between a first side 340 and an opposing second side 342. Mask plate 330 has a length and width that allows mask plate 330 to cover the bottom mouths 186 of the calibration sample bays 120 it is intended to cover. Mask plate 330 can have the same length and width as securing member 302, if desired. The thickness of mask plate 330 must be such that the mask plate 330 will not come into contact with objective 109. Accordingly, mask plate 330 can have a thickness between about 0.15 mm to about 1 mm, with about 0.5 mm to about 0.75 mm being common. Other thicknesses can also be used.

Mask plate 330 includes one or more apertures 344 extending completely therethrough between the top and bottom surfaces 332 and 334. Apertures 344 are formed on mask plate 330 such that when mask plate 330 is secured to bottom surface 128 of stage plate 125, each of the apertures 344 is positioned directly below a separate calibration sample bay 120. As a result, during use, fluorescent light emanating from the calibration sample 200 disposed within the calibration sample bay 120 passes through the corresponding aperture 344 so as to be imaged by the objective 109 when the objective 109 is aligned with calibration sample bay 120. Apertures 344 are typically circularly shaped, but other shapes are also possible.

Apertures 344 can vary in diameter but are typically smaller than the mouth 186 of calibration sample bay 120 so as to prevent anything that is disposed within calibration sample bay 120, such as calibration sample 200, from passing therethrough. In some embodiments, aperture 344 is sized so as to be larger than the field of view of the objective 109. For example, the diameter of aperture 344a shown in FIG. 17 can vary between about 4 mm to about 15 mm with about 5 mm to about 10 mm being common. Other diameters can also be used. In other embodiments, aperture 344 is very small so as to be used as a fiduciary mark 346 to be used for calibrating the positioning of the objective 109 in relation to the stage assembly. For example, the diameter of aperture 344b shown in FIG. 17 can be less than 2 mm or less than 1 mm. Because the fiduciary mark 346 is so small, the objective 109 can use it to determine and correct the focus, depth, and horizontal position deviations of the stage 118 with respect to the microscope, among other things. As shown in FIG. 17, different sizes of apertures 344 can be used in the same mask plate 330.

Mask plate 330 can be comprised of the same types of materials listed above regarding the securing member 302. In some embodiments, mask plate 330 comprises the same material as is used in securing member 302, although this is not necessary.

The first step in assembling stage assembly 300 to include calibration sample 200 within calibration sample bay 120, is securing the mask plate 330 to the bottom surface 128 of stage plate 125. This can be done by screws, adhesives, or any other method of securing. Whichever method is used must not prevent objective 109 from freely moving under the mask plate 330. Next, the calibration sample 200 is inserted into the calibration sample bay 120 through the upper mouth 188 and positioned at the bottom of calibration sample bay 120 so that the bottom surface 206 of calibration sample 200 is adjacent to the top surface 332 of mask plate 330. Next, a spacer plug 350 is inserted into the calibration sample bay 120 through the upper mouth 188 and positioned above and adjacent to the top surface 204 of calibration sample 200. Spacer plug 350 is used to help calibration sample 200 remain at the bottom of calibration sample bay 120 adjacent to mask plate 330. Spacer plug 350 is typically made of foam or cork, but any material that will cause calibration sample 200 to remain positioned adjacent to mask plate 330 and that does not photoreact with calibration sample 200 can be used. Finally, securing member 302 is positioned above the calibration sample bays 120 as discussed above and secured to the upper surface 155 of specimen plate holder 122. Because of securing member 302 and mask plate 330, spacer plug 350 and calibration sample 200 remain secured within calibration sample bay 120 without spacer plug 350 or calibration sample 200 needing to be adhered or otherwise attached to each other or to the securing member 302 or to mask plate 330.

In some embodiments, spacer plug 350 is attached or adhered to securing member 302 and in some of those embodiments calibration sample 200 is also adhered to spacer plug 350. In these latter embodiments, mask plate 330 can be omitted if desired, as calibration sample 200 will remain secured within calibration sample bay 120 via adherence of calibration sample 200 to spacer plug 350 which is adhered to securing member 302.

To replace any of the components disposed within any of the calibration sample bays 120, securing member 302 simply needs to be removed and the components removed from calibration sample bays through the mouths 188 thereof. Replacement components can then be inserted into calibration sample bays 120 through mouths 188 and the securing member 302 re-attached to the upper surface 155 of specimen plate holder 122.

Often when performing HCS, screenings are performed on a plurality of imaging systems and then correlated with each other. In those cases, it is desirable to be able to calibrate each imaging system with respect to each other and/or to adjust the results of the screenings so as to normalize the results with respect to all of the imaging systems. This can be done with the present invention.

Figure 18:
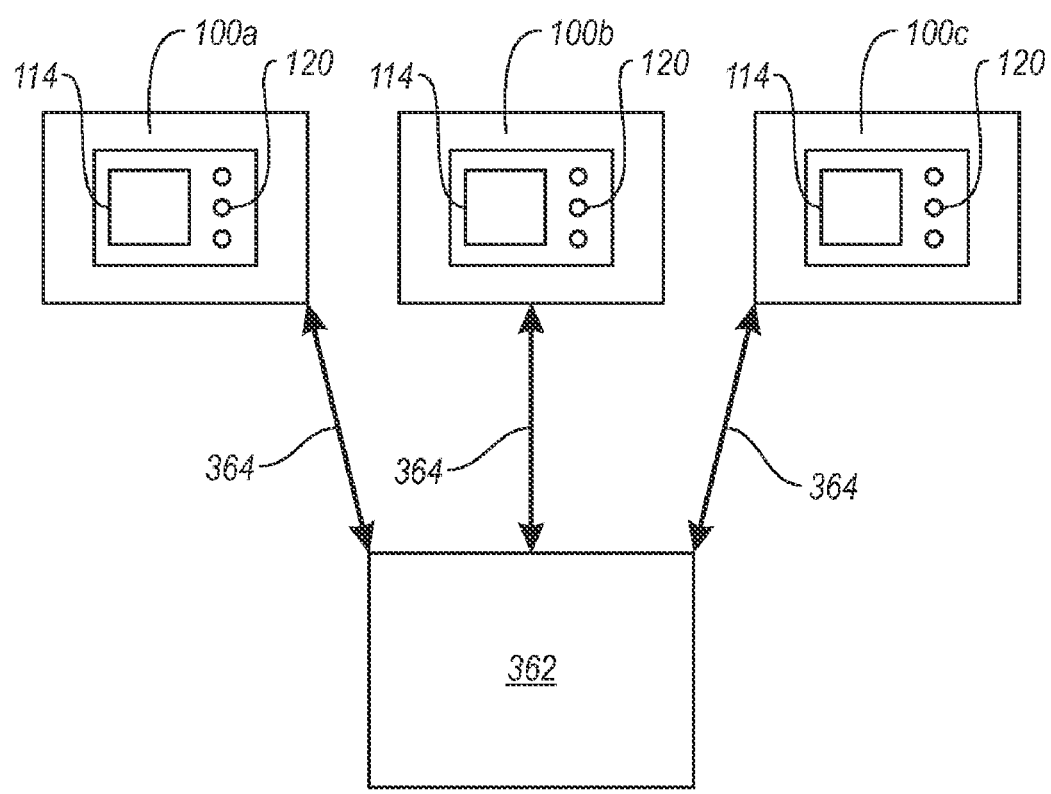
FIG. 18 is a block diagram of an HCS system having a plurality of imaging systems.

FIG. 18 shows a high content screening system 360 having a plurality of imaging systems 100a-c corresponding to the imaging system 100 described herein. High content screening system 360 also includes a computing device 362, such as a personal computer or the like, electronically connected to imaging systems 100a-c via one or more communications links 364. Each of the imaging systems 100 includes a stage assembly 114 with one or more calibration sample bays 120 and is thus able to be calibrated as discussed above. Once each imaging system 100 is calibrated, the results of the individual calibrations for each imaging system 100 are communicated to the computing device 362, which correlates the results of each imaging system 100 to the other imaging systems 100. This calibration information can then be used to further calibrate the individual imaging systems to match each other. Alternatively, the computing device 362 can store the calibration information for each imaging system and use that information to normalize the data that is obtained from each screening so that the screening data will be correlated with screening data obtained at the other imaging systems 100. For example, the imaging systems 100 can include the same color beads 280 (see FIG. 13), allowing software residing on the computing device 362 to compensate for variability in the light source from imaging system to imaging system, thereby allowing normalization of results between imaging systems.

It is appreciated that other arrangements or types of calibration sample bays, calibration samples, and/or securing devices can alternatively be used. For example, in addition to being formed in the stage plate or the specimen plate holder, the calibration sample bay can also be formed in the specimen plate itself. For example, calibration sample bays could be formed on an edge of the specimen plate or between wells. Having a calibration sample bay on the specimen plate may be desirable, for example, when calibrating the position of the wells in relation to the objective. In that case, a fiduciary mark or other position calibration sample could be used. Other fiduciary marks could also be formed on the specimen plate.

As another example, an active sample can be used as an alternative calibration sample. By active, it is meant that a sample having its own power source may be used. In such a case a small battery or the like may be included within the calibration sample. This could be used to power an emission filter wheel to test emission filter bands. As another example, a liquid calibration sample can be used that is pipetted into calibration sample bay 120 from above. In those embodiments, a glass plug or the like would remain at the bottom of the calibration sample bay 120 to prevent the liquid calibration sample from passing completely through the calibration sample bay 120. In still other embodiments, multiple colors can be represented in the same calibration sample. In other embodiments, calibration samples can be constructed so as to represent different portions of a cell so that calibrations of cell reading can be performed. Other alternatives can also be used.

Having one or more calibration sample bays disposed on a stage and able to each receive a different calibration sample gives the user many benefits over current apparatuses and methods of calibration. For example, because the calibration sample bays are disposed on the stage apart from the opening that receives the specimen plate, the imaging system calibrations can be performed without a separate specimen plate needing to be inserted into the imaging system, as is currently done. As a result, the calibrations can be performed regardless of whether a specimen plate is positioned on the specimen plate holder. Because of this, not only can calibrations of the imaging system be performed before an HCS screening, but they can also be performed during an HCS screening without having to remove the specimen plate from within the imaging system. That is, calibrations can be performed while the specimen plate remains installed within the stage housing. Furthermore, the calibrations can be performed without user intervention. This results in a savings of time and money, as well as reduces the number of potential errors that can occur as a result of removing and reinserting the specimen plate.

Figure 19:
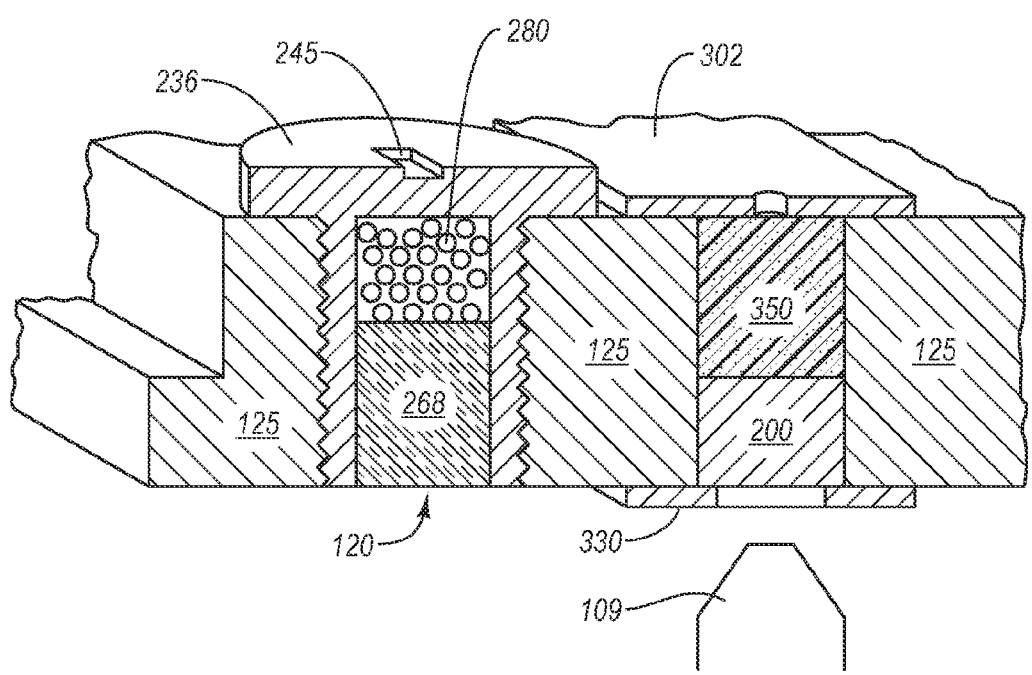
FIG. 19 is a cross sectional view of a stage assembly incorporating different types of calibration samples within different calibration sample bays.

Furthermore, in those systems having multiple calibration sample bays, various different calibrations or types of calibrations can also be performed without requiring calibration samples to be removed and replaced. For example, as discussed previously, when performing HCS scanning, calibration of different color wavelengths is oftentimes required. To facilitate this, calibration samples corresponding to the different wavelengths can all be concurrently disposed within the different calibration sample bays and used when needed. As another example, the calibration sample bays may contain different types of calibration samples calibration insert housings and/or methods of securing the calibration samples within the calibration sample bays, as shown in FIG. 19. In one embodiment a calibration sample comprising a photobleaching fluorescent material can be installed in one of the calibration sample bays 120 and a second calibration sample comprising a non-photo-bleaching fluorescent material can be installed in another calibration sample bay 120.

With the current invention, different types of calibrations can be performed manually or automatically, singly or at select intervals, with or without user intervention. For example, at startup various system parameters can be automatically calibrated, such as horizontal and vertical positioning. Then, during HCS scanning, these or other parameters can be periodically checked and calibrated. When a new type of scan is being performed, color parameters can be checked and calibrated. All of these different checks and calibrations can be done by user selection or automatically using software in a computing device, such as computing device 362. If desired, the user can automatically be notified whenever a calibration is performed or only when a calibration yields a system parameter outside of a predetermined value. Results can include the actual measured values or simply a pass/fail indication. Other types of information can also be communicated to the user.

In one method of calibrating an imaging system according to the present invention, the following is performed either during startup of the system or during use. First, a calibration sample corresponding to a particular system property or properties, such as any of the calibration samples discussed above, is positioned within a calibration sample bay disposed on the stage assembly. Positioning of the calibration sample can be done by threaded connection, press-fit connection, adhesive connection, or by using a calibration sample insert or securing member, or by any other method discussed above or otherwise encompassed by the present application. As discussed above, the calibration sample bay is spaced apart from the opening formed in stage assembly configured to receive a specimen plate. Typically, the calibration sample is installed in the calibration sample bay when the stage assembly is in the retracted position shown in FIG. 2. This step and/or any of the ones that follow can be performed while a specimen plate having biological cells is disposed within the opening in the stage assembly or while opening is empty.

The stage assembly is then inserted into the stage housing through the slot formed therein, if required. The stage assembly is then moved with respect to the microscope until the calibration sample bay is aligned with the objective of the imaging system, as shown, e.g., in FIG. 15.

One or more images of the calibration sample disposed within the calibration sample bay is then captured using the objective. The captured images are processed based on the system property or properties being calibrated to determine the results of the calibration. This processing is typically performed by a computing device, such as a personal computer or other computing device. During processing, the captured image and data derived therefrom can be compared to standard or desired values to determine deviations therefrom. For optic properties, such as flatness of field, the data can be compared to desired values. For control properties, such as horizontal positioning, an algorithm, as is known in the art, can be used.

The system property or properties of the imaging system corresponding to the calibration sample is then adjusted based on the calibration results. This can be done by modifying values in software, or by performing hardware revisions, depending on the property being adjusted, as is known in the art.

If desired, once the calibration sample has been positioned within the calibration sample bay, the rest of the steps can be periodically repeated as often as desired during HCS scanning to make sure the system properties remain calibrated.

When it is desired to replace the calibration sample, the calibration sample is removed from the calibration sample bay and a second calibration sample is then positioned within the calibration sample bay. Both of these steps are typically performed after the stage assembly has once again been placed in the retracted position shown in FIG. 2.

If more than one calibration sample bay is used on the same stage assembly, the above method can also be performed, wholly or in part, using the other calibration sample bay(s). For example, calibration sample(s) can be positioned in the other calibration sample bay(s) at the same time as the original, or anytime thereafter. And the rest of the steps recited above can be performed at any time in conjunction with or separately from the original calibration sample bay.

Furthermore, if more than one imaging system is used, the multiple imaging systems can also be calibrated with respect to each other. To do so, the above method is performed on each imaging system, then the results from each system are compared at a computing device and the HCS data obtained from each of the imaging systems is adjusted based on the system comparisons. In this manner, data from HCS scanning obtained using different imaging systems can be correlated and compared.

In another method of using an imaging system for high content screening of biological cells, the stage assembly of the imaging system is moved to a first position in which one of the wells of the specimen plate is aligned with the objective of the imaging system to allow an image of biological material disposed within the well to be captured. While the stage assembly is in this first position, the specimen plate is removably disposed on the stage assembly.

Next, the stage assembly is moved to a second position in which the calibration sample bay is aligned with the objective to allow an image of the calibration sample disposed within the calibration sample bay to be captured. As discussed above, the calibration sample bay is formed on the stage assembly and is spaced apart from the specimen plate.

If a second calibration sample bay is incorporated on the stage assembly, the stage assembly can be moved to a third position in which the second calibration sample bay is aligned with the objective to allow an image of the second calibration sample disposed within the second calibration sample bay to be captured. Similar to the original calibration sample bay discussed above, the second calibration sample bay is also formed on the stage assembly and is also spaced apart from the specimen plate. If more calibration sample bays are incorporated on the stage assembly, this step can be repeated for each calibration sample bay.

Where possible, any of the steps discussed above can be performed without user intervention using a computing device. Furthermore, the processes can be fully or partially automated.

The present invention may be embodied in other specific forms without departing from its spirit or essential characteristics. Accordingly, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A stage assembly for use in a high content screening system, the stage assembly comprising:
    a stage having a top surface and an opposing bottom surface, the stage bounding an opening extending between the top and bottom surfaces;
    a specimen plate holder removably positioned within the opening, the specimen plate holder being configured to receive a microtiter plate holding a plurality of biological cells;
    first and second calibration sample bays respectively formed on the stage at first and second locations spaced apart from the opening;
    first and second calibration samples removably secured within the first and second calibration sample bays respectively, one of the first and second calibration samples comprising a photo-bleaching fluorescent material and the other of the first and second calibration samples comprising a non-photo-bleaching fluorescent material.

2. The stage assembly as recited in claim 1, wherein the first calibration sample bay extends between the top and bottom surfaces of the stage.

3. The stage assembly as recited in claim 2, further comprising a securing member removably disposed on the top surface of the stage above the first calibration sample bay, the securing member having a plug secured thereto that extends into the first calibration sample bay.

4. The stage assembly as recited in claim 3, further comprising a mask plate disposed on the bottom surface of the stage, the mask plate bounding an aperture disposed directly below the first calibration sample bay, the aperture extending completely through the mask plate.

5. The stage assembly as recited in claim 1, comprising a plurality of calibration sample bays formed on the stage at a location spaced apart from the opening.

6. The stage assembly as recited in claim 5, wherein the calibration sample bays are aligned in a single row.

7. The stage assembly as recited in claim 5, wherein the calibration sample bays are formed in multiple rows.

8. The stage assembly as recited in claim 1, wherein the stage comprises a stage plate that bounds the opening, the first calibration sample bay being formed on the stage plate.

9. The stage assembly as recited in claim 1, wherein the stage comprises:
    a stage plate that bounds the opening; and
    the first calibration sample bay is at least partially formed on the specimen plate holder.

10. The stage assembly as recited in claim 1, further comprising a mask plate disposed on the bottom surface of the stage, the mask plate bounding an aperture disposed directly below the first calibration sample bay, the aperture extending completely through the mask plate.

11. The stage assembly as recited in claim 1, wherein an entire perimeter of the opening is bounded by the stage in an unbroken manner.

12. An imaging system for use in a high content screening system, the imaging system comprising:
    a stage housing;
    a stage assembly disposed on the stage housing, the stage assembly comprising:
        a stage having a top surface and an opposing bottom surface, the stage bounding an opening extending between the top and bottom surfaces, the opening being configured to receive a microtiter plate holding a plurality of biological cells; and a calibration sample bay formed on the stage at a location spaced apart from the opening, the calibration sample bay being configured to receive a calibration sample that is used to calibrate the imaging system;

a microscope having an objective through which information from the stage assembly is captured, the objective being positioned below the stage assembly; and one or more motors that move the stage assembly with respect to the objective, such that the stage assembly is moveable between a first position where at least a portion of the opening is disposed directly above the objective, and a second position where the calibration sample bay is disposed directly above the objective.

13. The imaging system as recited in claim 12, further comprising a microtiter plate disposed within the opening of the stage.

14. The imaging system as recited in claim 13, wherein the microtiter plate has a plurality of wells, biological cells being disposed within one or more of the wells.

15. The imaging system as recited in claim 12, further comprising a calibration sample removably disposed within the calibration sample bay.

16. The imaging system as recited in claim 15, wherein the calibration sample comprises a material that when viewed through the objective allows calibration of at least one of: focus, vertical offset, horizontal offset, intensity, flatness of field, distortion, contrast, and resolution of the imaging system.

17. The stage assembly as recited in claim 12, wherein the imaging system further comprises an enclosed chamber and the stage is configured to slide in and out of the enclosed chamber such that the stage is disposed within the enclosed chamber when the stage assembly is moved to the first position.

18. A high content screening system, comprising:
a plurality of imaging systems, each imaging system comprising:
a stage housing;
a stage assembly disposed on the stage housing, the stage assembly comprising:
a stage having a top surface and an opposing bottom surface, the stage bounding an opening extending between the top and bottom surfaces, the opening being configured to receive a microtiter plate holding a plurality of biological cells; and
a calibration sample bay formed on the stage at a location spaced apart from the opening, the calibration sample bay being configured to receive a calibration sample that is used to calibrate the imaging system;
a microscope having an objective through which information from the stage assembly is captured, the objective being positioned below the stage assembly; and
one or more motors that move the stage assembly with respect to the objective, such that the stage assembly is moveable between a first position where at least a portion of the opening is disposed directly above the objective, and a second position where the calibration sample bay is disposed directly above the objective; and
a computing device that calibrates the imaging systems with respect to each other based on measurements obtained from each imaging system using the calibration sample bays.

19. A high content screening system, comprising:
a plurality of imaging systems, each imaging system comprising:
a stage housing;
a stage assembly disposed on the stage housing, the stage assembly comprising:
a stage having a top surface and an opposing bottom surface, the stage bounding an opening extending between the top and bottom surfaces, the opening being configured to receive a microtiter plate holding a plurality of biological cells; and
a calibration sample bay formed on the stage at a location spaced apart from the opening, the calibration sample bay being configured to receive a calibration sample that is used to calibrate the imaging system;
a microscope having an objective through which information from the stage assembly is captured, the objective being positioned below the stage assembly; and
one or more motors that move the stage assembly with respect to the objective, such that the stage assembly is moveable between a first position where at least a portion of the opening is disposed directly above the objective, and a second position where the calibration sample bay is disposed directly above the objective; and
a computing device that normalizes data values obtained from the imaging systems based on measurements obtained from each imaging system using the calibration sample bays.

20. A method of using an imaging system for high content screening of biological cells, the method comprising:
moving a stage assembly of an imaging system to a first position in which a well is aligned with an objective of the imaging system to allow an image to be captured of biological material disposed within the well, the well being disposed within a microtiter plate removably disposed on a specimen plate holder which is removably positioned on the stage assembly;
moving the stage assembly to a second position in which a first calibration sample bay is aligned with the objective to allow an image to be captured of a first calibration sample disposed within the first calibration sample bay, the first calibration sample bay being formed on the stage assembly and spaced apart from the specimen plate; and
moving the stage assembly to a third position in which a second calibration sample bay is aligned with the objective to allow an image to be captured of a second calibration sample disposed within the second calibration sample bay, the second calibration sample bay also being formed on the stage assembly and being spaced apart from the microtiter plate.

21. The method as recited in claim 20, wherein the first calibration sample bay is above the objective when the stage assembly is in the second position.

22. A method of calibrating an imaging system used for high content screening of biological cells, the method comprising:
positioning a first calibration sample in a calibration sample bay of a stage assembly of an imaging system, the calibration sample bay being spaced apart from an opening in the stage assembly configured to receive a microtiter plate;
moving the stage assembly so that the calibration sample bay is aligned above an objective of the imaging system;
capturing an image of the first calibration sample disposed within the calibration sample bay using the objective;
processing the captured image to determine calibration results;
adjusting system parameters of the imaging system based on the calibration results;
removing the first calibration sample from the calibration sample bay; and positioning a second calibration sample in the calibration sample bay.

23. The method as recited in claim 22, wherein the recited acts are performed at a startup of the imaging system before a microtiter plate having biological cells is disposed within the opening in the stage assembly.

24. The method as recited in claim 22, wherein the acts of moving the stage, capturing an image, processing the captured image, and adjusting system parameters are performed while a microtiter plate having biological cells is disposed within the opening in the stage assembly.

25. The method as recited in claim 22, wherein processing the captured image comprises determining measurements of at least one of: intensity, flatness of field, distortion, contrast, and resolution of the imaging system.

26. The method as recited in claim 22, wherein the acts of moving the stage, capturing an image, processing the captured image, and adjusting system parameters are periodically performed during high content screening of cells.

27. The method as recited in claim 22, wherein a specimen plate holder is removably positioned at least partially within the opening of the stage assembly, the specimen plate holder being configured to receive a microtiter plate.

28. A method of calibrating a plurality of imaging systems with respect to each other, the imaging systems being used for high content screening of biological cells, the method comprising:
 for each imaging system, calibrating the imaging system by:
  positioning a calibration sample in a calibration sample bay of a stage assembly of the imaging system, the calibration sample bay being spaced apart from an opening in the stage assembly configured to receive a microtiter plate;
  moving the stage assembly so that the calibration sample bay is aligned above an objective of the imaging system;
  capturing an image of the calibration sample disposed within the calibration sample bay using the objective;
  processing the captured image to determine calibration results; and
  adjusting system parameters of the imaging system based on the calibration results; and
 adjusting the results of high content screening of each imaging system so as to normalize the results with respect to all of the imaging systems.

* * * * *